(12) United States Patent
Flatt et al.

(10) Patent No.: US 11,292,135 B2
(45) Date of Patent: Apr. 5, 2022

(54) ROTATING SWITCH SENSOR FOR A ROBOTIC SYSTEM

(71) Applicant: MAKO Surgical Corp., Ft. Lauderdale, FL (US)

(72) Inventors: James E. Flatt, Kalamazoo, MI (US); Philip Robert Woods, Kalamazoo, MI (US); Cory J. Welch, Plainwell, MI (US); Mark A. Wasserman, Delton, MI (US)

(73) Assignee: MAKO Surgical Corp., Ft. Lauderdale, FL (US)

( * ) Notice: Subject to any disclaimer, the term of this patent is extended or adjusted under 35 U.S.C. 154(b) by 474 days.

(21) Appl. No.: 16/428,341

(22) Filed: May 31, 2019

(65) Prior Publication Data

US 2019/0366550 A1 Dec. 5, 2019

Related U.S. Application Data

(60) Provisional application No. 62/678,838, filed on May 31, 2018.

(51) Int. Cl.
*B25J 9/16* (2006.01)
*B25J 9/00* (2006.01)
(Continued)

(52) U.S. Cl.
CPC .......... *B25J 9/1694* (2013.01); *B25J 9/0096* (2013.01); *B25J 9/1628* (2013.01); *B25J 9/1651* (2013.01);
(Continued)

(58) Field of Classification Search
CPC . A61B 17/2841; A61B 17/1622; A61B 34/30; A61B 17/14; A61B 34/74;
(Continued)

(56) References Cited

U.S. PATENT DOCUMENTS

| 3,046,361 A | 7/1962 | Wiehl |
| 4,541,771 A | 9/1985 | Beni et al. |

(Continued)

FOREIGN PATENT DOCUMENTS

| WO | 2010013992 A1 | 2/2010 |
| WO | 2017176275 A1 | 10/2017 |

*Primary Examiner* — Abby Y Lin
*Assistant Examiner* — Dylan M Katz
(74) *Attorney, Agent, or Firm* — Howard & Howard Attorneys PLLC

(57) ABSTRACT

A sensor system includes a first member extending along a rotational axis and having a surface disposed circumferentially about the axis. The sensor system further includes a conductive element fixed to the first member and disposed on the surface and about the rotational axis and a second member extending along the axis. A rotational position between the first member and the second member is adjustable. The sensor system further includes a target mounted to and rotatable with the second member and being movable relative to the second member between first and second positions. The target is spaced apart from the conductive element in both the first and second positions and is closer to the conductive element in the second position compared to the first position. The conductive element is configured to sense the target in the second position for any rotational position between the first member and the second member.

29 Claims, 14 Drawing Sheets

(51) Int. Cl.
    *B25J 19/02* (2006.01)
    *B25J 13/02* (2006.01)
    *A61B 34/30* (2016.01)
    *A61B 17/28* (2006.01)
    *A61B 17/16* (2006.01)

(52) U.S. Cl.
    CPC ............ *B25J 13/02* (2013.01); *B25J 19/027* (2013.01); *A61B 17/1622* (2013.01); *A61B 17/2841* (2013.01); *A61B 34/30* (2016.02)

(58) Field of Classification Search
    CPC .............. A61B 17/16; A61B 2034/101; A61B 2034/2055; A61B 2017/00367; B25J 9/1694; B25J 9/0096; B25J 9/1628; B25J 9/1651; B25J 13/02; B25J 19/027; B25J 15/0019; G05G 2009/04755
    See application file for complete search history.

(56) References Cited

U.S. PATENT DOCUMENTS

| | | |
|---|---|---|
| 4,950,987 A | 8/1990 | Vranish et al. |
| 5,098,024 A | 3/1992 | MacIntyre et al. |
| 5,404,101 A | 4/1995 | Logue |
| 5,432,444 A | 7/1995 | Yasohama et al. |
| 5,559,432 A | 9/1996 | Logue |
| 5,617,023 A | 4/1997 | Skalski |
| 5,909,118 A | 6/1999 | Logue |
| 5,911,627 A | 6/1999 | Piot et al. |
| 5,939,878 A | 8/1999 | Dong |
| 5,946,198 A | 8/1999 | Hoppe et al. |
| 6,424,145 B1 | 7/2002 | Woolsey et al. |
| 6,587,750 B2 | 7/2003 | Gerbi et al. |
| 7,095,198 B1 | 8/2006 | O'Brien |
| 7,944,433 B2 | 5/2011 | Schena et al. |
| 8,035,233 B2 | 10/2011 | Leedy |
| 8,273,087 B2 * | 9/2012 | Kimura .......... A61B 17/320068 606/79 |
| 9,008,757 B2 | 4/2015 | Wu |
| 9,119,655 B2 | 9/2015 | Bowling et al. |
| 9,566,121 B2 | 2/2017 | Staunton et al. |
| 9,937,058 B2 | 4/2018 | Axelson, Jr. et al. |
| 2003/0060927 A1 | 3/2003 | Gerbi et al. |
| 2009/0030428 A1 | 1/2009 | Omori et al. |
| 2012/0030429 A1 | 2/2012 | Synge |
| 2014/0276949 A1 | 9/2014 | Staunton et al. |
| 2016/0256162 A1 | 9/2016 | Shelton, IV et al. |
| 2018/0110572 A1 | 4/2018 | Flatt |

\* cited by examiner

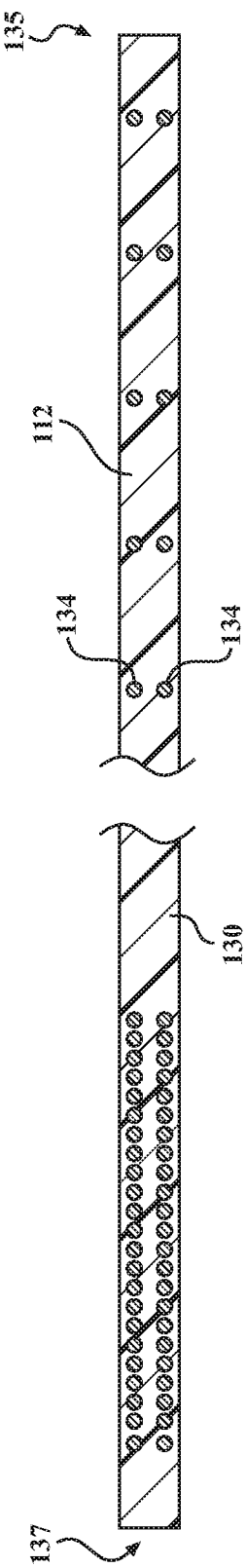

ROTATING SWITCH SENSOR FOR A ROBOTIC SYSTEM

RELATED APPLICATIONS

This application claims priority to and the benefit of U.S. Provisional Patent Application No. 62/678,838, filed on May 31, 2018, the entire contents of which are hereby incorporated by reference.

TECHNICAL FIELD

The present disclosure relates generally to a sensor system having a conductive element mounted to a first member and a target mounted to a second member, with a rotational position between the first and second members being adjustable.

BACKGROUND

Robotic systems are commonly used to perform surgical procedures and typically include a robot comprising a robotic arm and an end effector coupled to an end of the robotic arm and presenting a tool. The end effector includes a handle for manipulating the position of the tool. The handle often includes a button in communication with a controller for manipulating certain operational characteristics of the end effector or the robotic arm.

In some conventional systems, the handle is in a fixed position relative to the end effector, i.e., the handle cannot rotate. While the handle does permit positioning of the tool, the positioning of the handle, and consequently the button, are not always suited for the surgeon's ergonomics throughout the range of motion of the robot, leading to fatigue and discomfort.

Handles that are rotatable about a fixed portion of the end effector have been contemplated. However, in some applications the button is directly wired to the fixed portion of the end effector, which limits the range of motion of the handle about the fixed portion. Furthermore, the handle cannot be readily disassembled from the end effector for cleaning and sterilization. In other applications, the button is not directly wired to the fixed portion. However, depressing the button ultimately causes physical contact with a stationary component on the fixed portion in order to send a signal to the controller, which results in friction between the handle and the fixed portion of the end effector. Such prior configurations potentially restrict movement of the handle, and include additional components that can fail during use or sterilization, thereby decreasing the longevity of the part.

As such, there is a need in the art for sensor systems that address at least the aforementioned problems.

SUMMARY

One example of a sensor system is provided. The sensor system comprises a first member extending along a rotational axis and having a surface disposed circumferentially about the rotational axis. The sensor system further comprises a conductive element fixed to the first member and disposed on the surface and disposed about the rotational axis. The sensor system further comprises a second member extending along the rotational axis. A rotational position between the first member and the second member is adjustable. The sensor system further comprises a target mounted to and rotatable with the second member and being movable relative to the second member between a first position and a second position. The target is spaced apart from the conductive element in both the first and second positions and is closer to the conductive element in the second position compared to the first position. The conductive element is configured to sense the target in the second position for any rotational position between the first member and the second member.

One example of an end effector for a robotic manipulator is provided. The end effector comprises the first member extending along the rotational axis and having the surface disposed circumferentially about the rotational axis. The end effector further comprises an energy applicator disposed within the first member. The end effector further comprises the conductive element fixed to the first member and disposed on the surface and disposed about the rotational axis. The end effector further comprises a handle extending along the rotational axis and with the rotational position between the first member and the handle being adjustable. The end effector further comprises the target mounted to and rotatable with the handle and being movable relative to the handle between the first position and the second position. The target is spaced apart from the conductive element in both the first and second positions and is closer to the conductive element in the second position compared to the first position. The conductive element is configured to sense the target in the second position for any rotational position between the first member and the handle.

One example of a robotic system is provided. The robotic system comprises a manipulator comprising a plurality of links and an end effector coupled to the manipulator. The end effector comprises the first member extending along the rotational axis and having the surface disposed circumferentially about the rotational axis. The end effector further comprises an energy applicator disposed within the first member. The end effector further comprises the conductive element fixed to the first member and disposed on the surface and disposed about the rotational axis. The end effector further comprises a handle extending along the rotational axis and with the rotational position between the first member and the handle being adjustable. The end effector further comprises the target mounted to and rotatable with the handle and being movable relative to the handle between the first position and the second position. The target is spaced apart from the conductive element in both the first and second positions and is closer to the conductive element in the second position compared to the first position. The conductive element is configured to sense the target in the second position for any rotational position between the first member and the handle.

Accordingly, the sensor system, end effector, and robotic system provide the advantage of permitting unrestricted rotational movement of the handle of the end effector for matching the ergonomics of an operator. Furthermore the spacing between the target and the conductive element does not add friction into the rotation of the handle and allows for easy disassembly of the handle and the target from the first member and the conductive element, which improves cleaning and sterilization of the end effector and improves longevity of the sensor system and end effector. Advantages and technical solutions of the sensor system, end effector, and robotic system other than those described above will be understood from the following description.

BRIEF DESCRIPTION OF THE DRAWINGS

Advantages of the present invention will be readily appreciated as the same becomes better understood by reference to the following detailed description when considered in connection with the accompanying drawings wherein:

FIG. 23 is a cross-sectional view of the conductive element shown in FIG. 22 taken along line 23-23.

DETAILED DESCRIPTION

I. Robotic System Overview

Referring to the Figures, wherein like numerals indicate like or corresponding parts throughout the several views, a robotic system 10 (hereinafter "system") is shown throughout.

Figure 1:
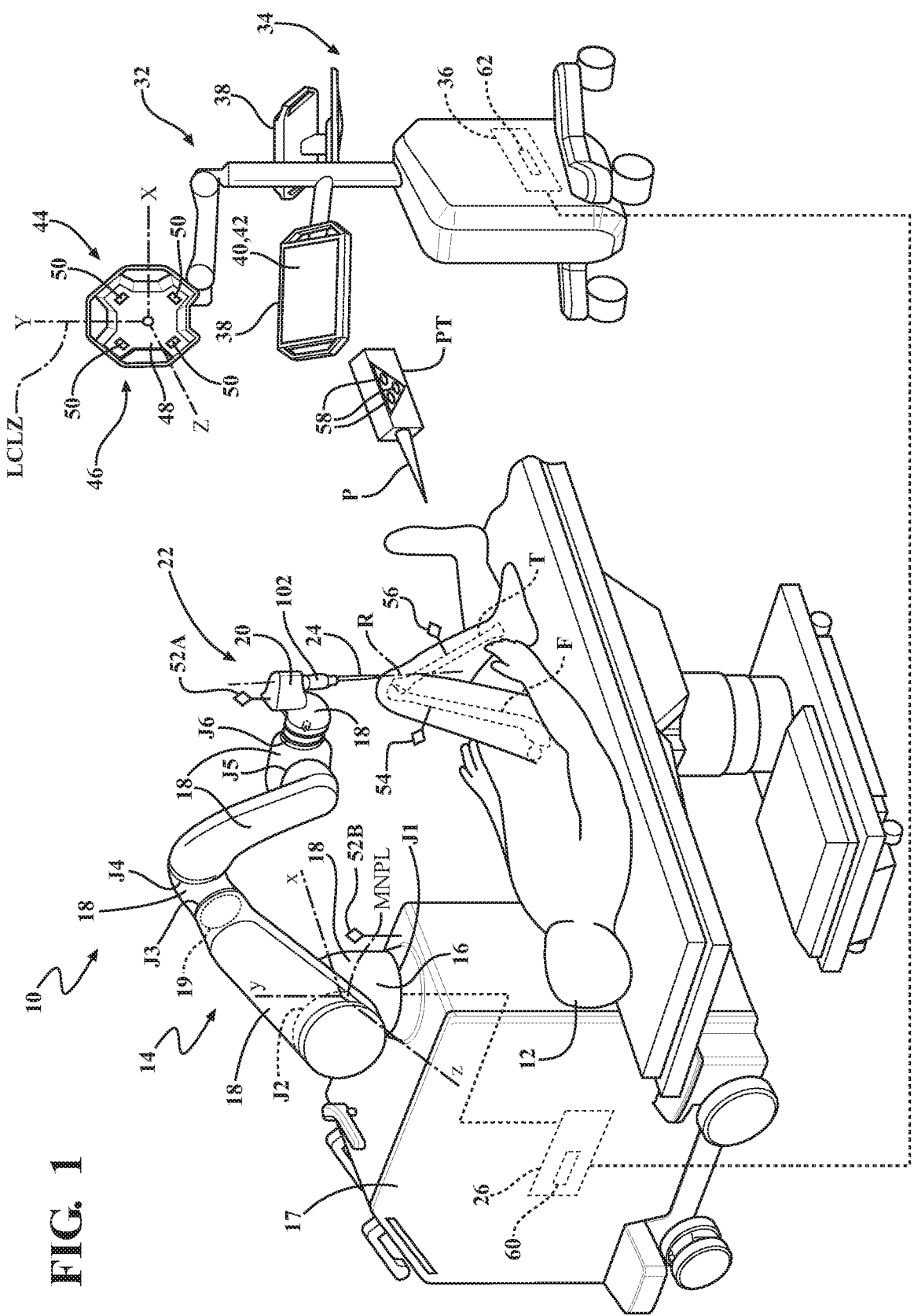
FIG. 1 is a perspective view of a robotic system for manipulating a target tissue of a patient with a tool, according to one example.

As shown in FIG. 1, the system 10 may treat an anatomy (surgical site) of a patient 12, such as bone or soft tissue. In FIG. 1, the patient 12 is undergoing a surgical procedure. The anatomy in FIG. 1 includes a femur (F) and a tibia (T) of the patient 12. The surgical procedure may involve tissue removal or treatment. Treatment may include cutting, coagulating, lesioning the tissue, treatment in place of tissue, or the like. In some examples, the surgical procedure involves partial or total knee or hip replacement surgery. In one example, the system 10 is designed to cut away material to be replaced by surgical implants, such as hip and knee implants, including unicompartmental, bicompartmental, multicompartmental, or total knee implants. Some of these types of implants are shown in U.S. Pat. No. 9,937,058, entitled, "Prosthetic Implant and Method of Implantation," the disclosure of which is hereby incorporated by reference. The system 10 and method disclosed herein may be used to perform other procedures, surgical or non-surgical, or may be used in industrial applications or other applications where robotic systems are utilized.

The system 10 includes a robotic manipulator 14. The robotic manipulator 14 has a base 16 and plurality of links 18. A manipulator cart 17 supports the robotic manipulator 14 such that the robotic manipulator 14 is fixed to the manipulator cart 17. The links 18 collectively form one or more arms of the robotic manipulator 14. The robotic manipulator 14 may have a serial arm configuration (as shown in FIG. 1) or a parallel arm configuration. In other examples, more than one robotic manipulator 14 may be utilized in a multiple arm configuration. The robotic manipulator 14 may comprise a plurality of (prismatic and/or rotating) joints (J) and a plurality of motor and/or joint encoders 19 located at the joints (J) for determining position data of the joints (J). For simplicity, only one joint encoder 19 is illustrated in FIG. 1, although it is to be appreciated that the other joint encoders 19 may be similarly illustrated. The robotic manipulator 14 according to one example has six joints (J1-J6) implementing at least six-degrees of freedom (DOF) for the robotic manipulator 14. However, the robotic manipulator 14 may have any number of degrees of freedom and may have any suitable number of joints (J) and redundant joints (J).

A surgical tool 20 (hereinafter "tool") couples to the robotic manipulator 14 and is movable relative to the base 16 to interact with the anatomy in certain modes. The tool 20 is or forms part of an end effector 22 in certain modes. The tool 20 may be grasped by the operator. One exemplary arrangement of the robotic manipulator 14 and the tool 20 is described in U.S. Pat. No. 9,119,655, entitled, "Surgical Manipulator Capable of Controlling a Surgical Instrument in Multiple Modes," the disclosure of which is hereby incorporated by reference. The robotic manipulator 14 and the tool 20 may be arranged in alternative configurations. The tool 20 can be like that shown in U.S. Pat. No. 9,566,121, filed on Mar. 15, 2014, entitled, "End Effector of a Surgical Robotic Manipulator," hereby incorporated by reference.

The positioning of the end effector 22 and the tool 20 is defined by the robotic manipulator 14. This positioning may not be ideally suited for the ergonomics of an operator. To that end, the end effector 22 may include a handle 102 that is rotatable about a rotational axis R. The rotatable handle 102 allows the operator to hold the tool 20 in the most comfortable position while the robotic manipulator 14 moves the tool 20 into the necessary position for robotic manipulation. Exemplary arrangements of the handle 102 rotatable about the rotational axis R are described in U.S. Pat. No. 9,566,121, entitled, "End Effector of a Surgical Robotic Manipulator," and U.S. Patent Application Publication No. 2018/0110572, filed on Oct. 21, 2016, entitled, "Systems and Tools for Use with Surgical Robotic Manipulators," the disclosures of which are hereby incorporated by reference.

The tool 20 includes an energy applicator 24 designed to contact the target site, such as the tissue of the patient 12 at the surgical site. The energy applicator 24 may be a drill, a saw blade, a bur, an ultrasonic vibrating tip, or the like.

Figure 2:
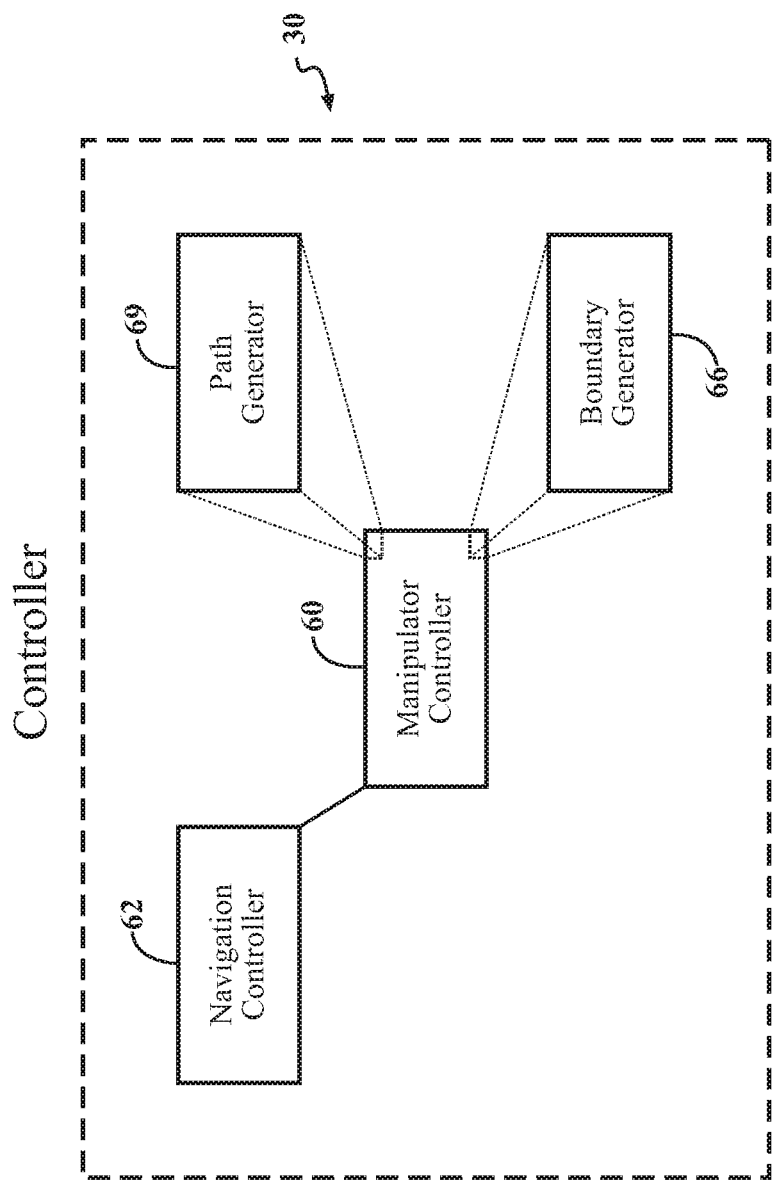
FIG. 2 is a block diagram of a controller for controlling the robotic system, according to one example.
Figure 3:
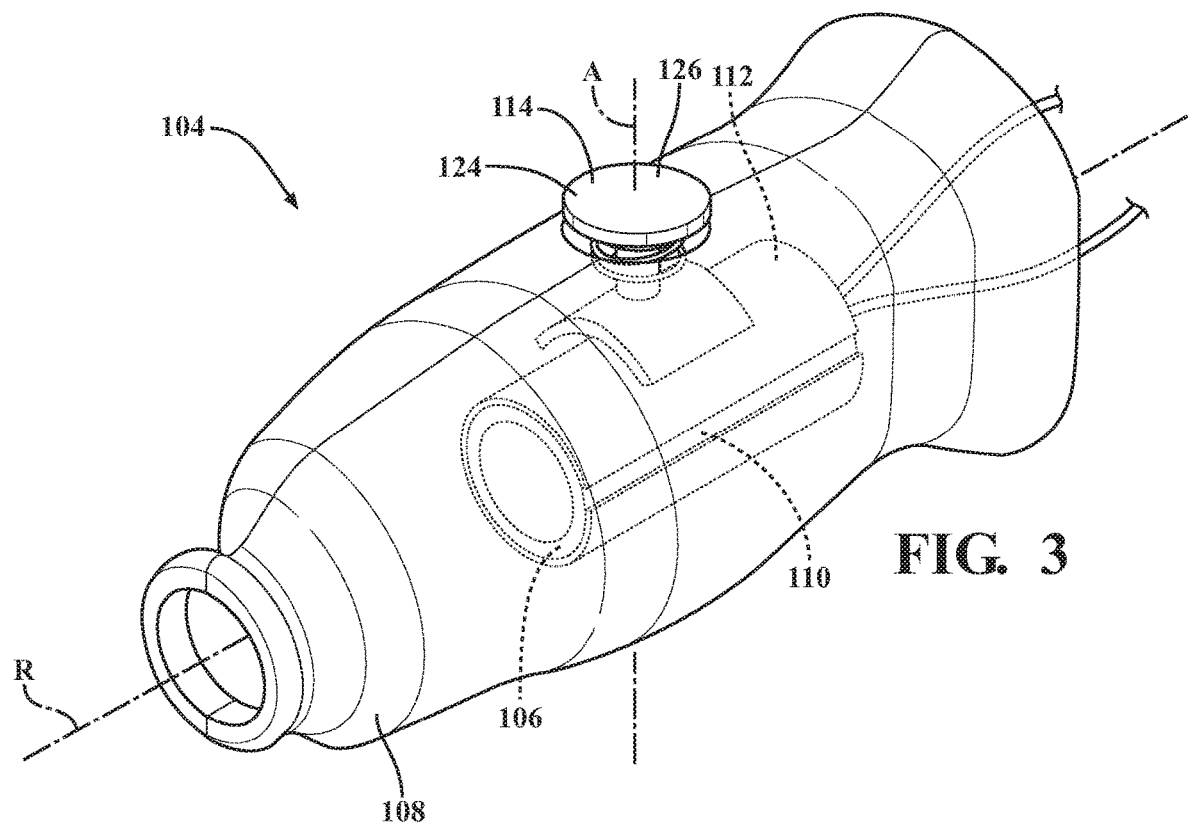
FIG. 3 is a perspective view of a sensor system showing a second member and a target, according to one example.
Figure 4:
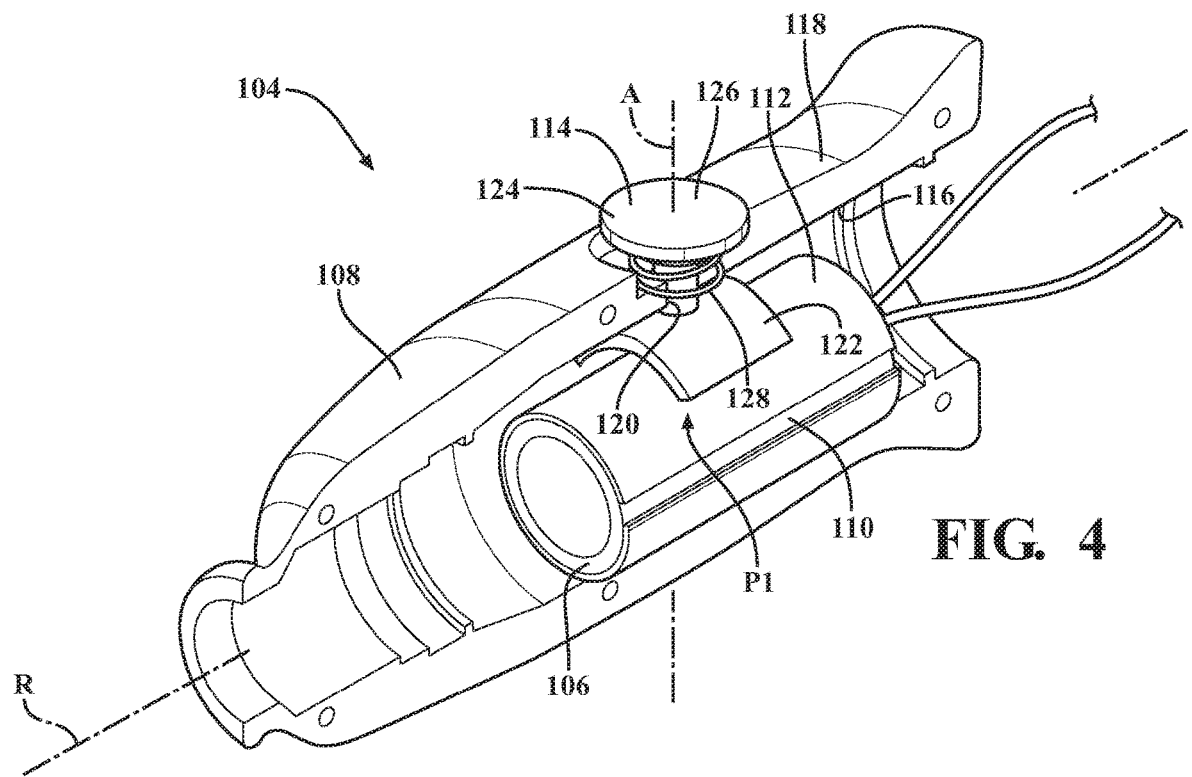
FIG. 4 is a perspective view of the sensor system shown in FIG. 3, with a portion of the second member removed to show a first member and a conductive element.
Figure 5:
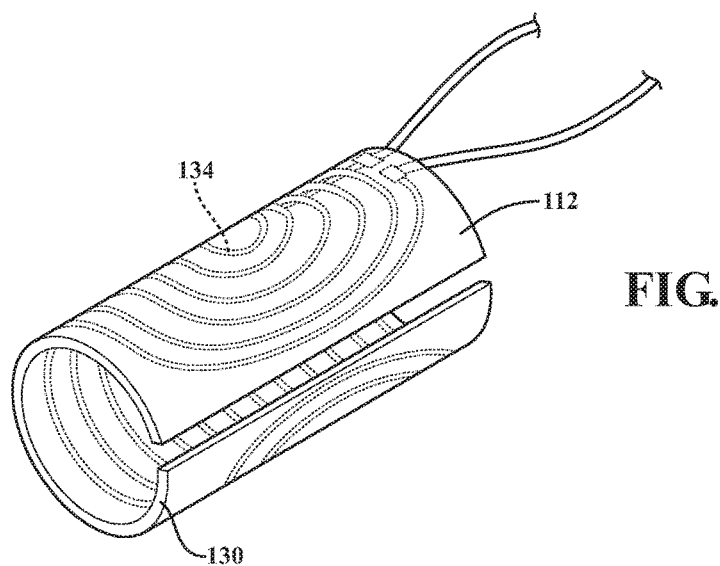
FIG. 5 is a perspective view of the conductive element comprising a conductive coil and a substrate, according to one example.
Figure 6:
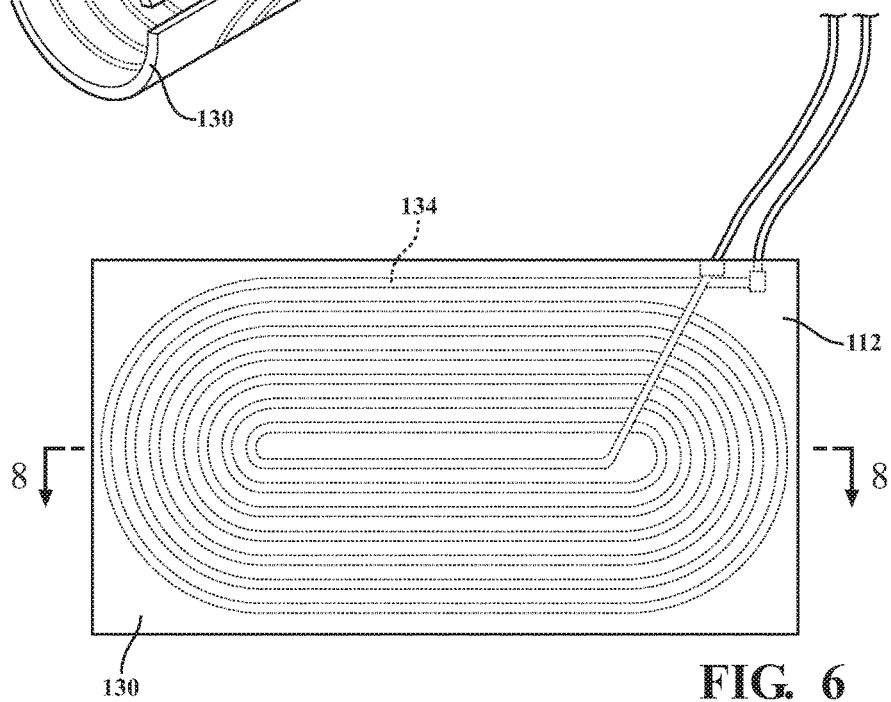
FIG. 6 is an elevational view of the conductive element shown in FIG. 5, unrolled into a planar configuration.
Figure 7:
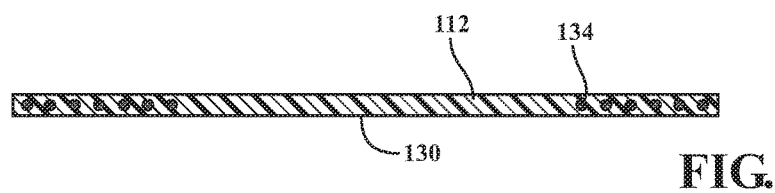
FIG. 7 is a cross-sectional view of the conductive element shown in FIG. 6 taken along line 7-7.

Referring to FIG. 2, the system 10 includes a controller 30. The controller 30 includes software and/or hardware for controlling the robotic manipulator 14. The controller 30 directs the motion of the robotic manipulator 14 and controls a state (position and/or orientation) of the tool 20 with respect to a coordinate system of the manipulator 14.

As shown in FIG. 1, the system 10 further includes a navigation system 32. One example of the navigation system 32 is described in U.S. Pat. No. 9,008,757, filed on Sep. 24, 2013, entitled, "Navigation System Including Optical and Non-Optical Sensors," hereby incorporated by reference. The navigation system 32 is configured to track movement of various objects. Such objects include, for example, the robotic manipulator 14, the tool 20 and the anatomy, e.g., femur F and tibia T. The navigation system 32 tracks these objects to gather state information of each object with respect to a (navigation) localizer coordinate system LCLZ. Coordinates in the localizer coordinate system LCLZ may be transformed to the manipulator coordinate system MNPL, and/or vice-versa, using transformation techniques described herein.

The navigation system 32 includes a cart assembly 34 that houses a navigation computer 36, and/or other types of control units. A navigation interface is in operative communication with the navigation computer 36. The navigation interface includes one or more displays 38. First and second input devices 40, 42 may be used to input information into the navigation computer 36 or otherwise to select/control certain aspects of the navigation computer 36. As shown in FIG. 1, such input devices 40, 42 include interactive touch-screen displays. However, the input devices 40, 42 may include any one or more of a keyboard, a mouse, a microphone (voice-activation), gesture control devices, and the like. The controller 30 may be implemented on any suitable device or devices in the system 10, including, but not limited to, the manipulator computer 26, the navigation computer 36, and any combination thereof.

The navigation system 32 also includes a navigation localizer 44 (hereinafter "localizer") coupled to the navigation computer 36. In one example, the localizer 44 is an optical localizer and includes a camera unit 46. The camera unit 46 has an outer casing 48 that houses one or more optical sensors 50.

The navigation system 32 includes one or more trackers. In one example, the trackers include a pointer tracker PT, one or more manipulator trackers 52, a first patient tracker 54, and a second patient tracker 56. In the illustrated example of FIG. 1, the manipulator tracker 52 is firmly attached to the tool 20 (i.e., tracker 52A), the first patient tracker 54 is firmly affixed to the femur F of the patient 12, and the second patient tracker 56 is firmly affixed to the tibia T of the patient 12. In this example, the patient trackers 54, 56 are firmly affixed to sections of bone. The pointer tracker PT is firmly affixed to a pointer P used for registering the anatomy to the localizer coordinate system LCLZ. The manipulator tracker 52 may be affixed to any suitable component of the robotic manipulator 14, in addition to, or other than the tool 20, such as the base 16 (i.e., tracker 52B), or any one or more links 18 of the robotic manipulator 14. The trackers 52, 54, 56, PT may be fixed to their respective components in any suitable manner.

Any one or more of the trackers may include active markers 58. The active markers 58 may include light emitting diodes (LEDs). Alternatively, the trackers 52, 54, 56 may have passive markers, such as reflectors, which reflect light emitted from the camera unit 46. Other suitable markers not specifically described herein may be utilized.

The localizer 44 tracks the trackers 52, 54, 56 to determine a state of each of the trackers 52, 54, 56, which correspond respectively to the state of the object respectively attached thereto. The localizer 44 provides the state of the trackers 52, 54, 56 to the navigation computer 36. In one example, the navigation computer 36 determines and communicates the state the trackers 52, 54, 56 to the manipulator computer 26. As used herein, the state of an object includes, but is not limited to, data that defines the position and/or orientation of the tracked object or equivalents/derivatives of the position and/or orientation. For example, the state may be a pose of the object, and may include linear data, and/or angular velocity data, and the like.

Although one example of the navigation system 32 is shown in the Figures, the navigation system 32 may have any other suitable configuration for tracking the robotic manipulator 14 and the patient 12. In one example, the navigation system 32 and/or localizer 44 are ultrasound-based. In another example, the navigation system 32 and/or localizer 44 are radio frequency (RF)-based.

The navigation system 32 and/or localizer 44 may have any other suitable components or structure not specifically recited herein. Furthermore, any of the techniques, methods, and/or components described above with respect to the camera-based navigation system 32 shown throughout the Figures may be implemented or provided for any of the other examples of the navigation system 32 described herein. For example, the navigation system 32 may utilize solely inertial tracking or any combination of tracking techniques.

As shown in FIG. 2, the controller 30 further includes software modules. The software modules may be part of a computer program or programs that operate on the manipulator computer 26, navigation computer 36, or a combination thereof, to process data to assist with control of the system 10. The software modules include instructions stored in memory on the manipulator computer 26, navigation computer 36, or a combination thereof, to be executed by one or more processors of the computers 26, 36. Additionally, software modules for prompting and/or communicating with the operator may form part of the program or programs and may include instructions stored in memory on the manipulator computer 26, navigation computer 36, or a combination thereof. The operator interacts with the first and second input devices 40, 42 and the one or more displays 38 to communicate with the software modules. The user interface software may run on a separate device from the manipulator computer 26 and navigation computer 36.

The controller 30 includes a manipulator controller 60 for processing data to direct motion of the robotic manipulator 14. In one example, as shown in FIG. 1, the manipulator controller is implemented on the manipulator computer 26. The manipulator controller 60 may receive and process data from a single source or multiple sources. The controller 30 further includes a navigation controller 62 for communicating the state data relating to the femur F, tibia T, and robotic manipulator 14 to the manipulator controller 60. The manipulator controller 60 receives and processes the state data provided by the navigation controller 62 to direct movement of the robotic manipulator 14. In one example, as shown in FIG. 1, the navigation controller 62 is implemented on the navigation computer 36. The manipulator controller 60 or navigation controller 62 may also communicate states of the patient 12 and robotic manipulator 14 to the operator by displaying an image of the femur F and/or tibia T and the robotic manipulator 14 on the one or more displays 38. The manipulator computer 26 or navigation computer 36 may also command display of instructions or request information using the display 38 to interact with the operator and for directing the robotic manipulator 14.

As shown in FIG. 2, the controller 30 includes a boundary generator 66. The boundary generator 66 is a software module that may be implemented on the manipulator controller 60. Alternatively, the boundary generator 66 may be implemented on other components, such as the navigation controller 62. The boundary generator 66 generates virtual boundaries for constraining the tool 20. Such virtual boundaries may also be referred to as virtual meshes, virtual constraints, or the like. The virtual boundaries may be defined with respect to a 3-D bone model registered to the one or more patient trackers 54, 56 such that the virtual boundaries are fixed relative to the bone model. The state of the tool 20 is tracked relative to the virtual boundaries. In one example, the state of the TCP is measured relative to the virtual boundaries for purposes of determining when and where haptic feedback force is applied to the robotic manipulator 14, or more specifically, the tool 20.

A tool path generator 69 is another software module run by the controller 30, and more specifically, the manipulator controller 60. The tool path generator 69 generates a path 100 for the tool 20 to traverse, such as for removing sections of the anatomy to receive an implant. One exemplary system and method for generating the tool path 100 is explained in U.S. Pat. No. 9,119,655, entitled, "Surgical Manipulator Capable of Controlling a Surgical Instrument in Multiple Modes," the disclosure of which is hereby incorporated by reference. In some examples, the virtual boundaries and/or tool paths 100 may be generated offline rather than on the manipulator computer 26 or navigation computer 36. Thereafter, the virtual boundaries and/or tool paths 100 may be utilized at runtime by the manipulator controller 60.

II. Rotatable Sensor System

Referring to the Figures, wherein like numerals indicate like or corresponding parts throughout the several views, a sensor system 104 is generally shown in FIGS. 3-18. The sensor system 104 comprises a first member 106 extending along the rotational axis R and having a surface 110 disposed circumferentially about the rotational axis R. The sensor system 104 further comprises a conductive element 112 fixed to the first member 106 and disposed on the surface 110 and about the rotational axis R.

The sensor system 104 further comprises a second member 108 extending along the rotational axis R. A rotational position between the first member 106 and the second member 108 is adjustable. The sensor system 104 further comprises a target 114 mounted to and rotatable with the second member 108 and being movable relative to the second member 108 between a first position P1 (shown in FIGS. 8 and 13) and a second position P2 (shown in FIGS. 9 and 14. The target 114 is spaced apart from the conductive element 112 in both the first and second positions P1, P2 and is closer to the conductive element 112 in the second position P2 compared to the first position P1. The conductive element 112 is configured to sense the target 114 in the second position P2 for any rotational position between the first member 106 and the second member 108.

In one example, the sensor system 104 is incorporated with the end effector 22 of the manipulator 14, as shown in FIGS. 15-18. The end effector 22 comprises the first member 106 extending along the rotational axis R and having the surface 110 disposed circumferentially about the rotational axis R. The end effector 22 further comprises the energy applicator 24 optionally disposed and rotatable within the first member 106. The end effector 22 further comprises the conductive element 112 fixed to the first member 106 and disposed on the surface 110 and about the rotational axis R.

The end effector 22 further comprises the handle 102 (i.e., the second member 108 of the sensor system 104) extending along the rotational axis R and with the rotational position between the first member 106 and the handle 102 being adjustable.

Figure 17:
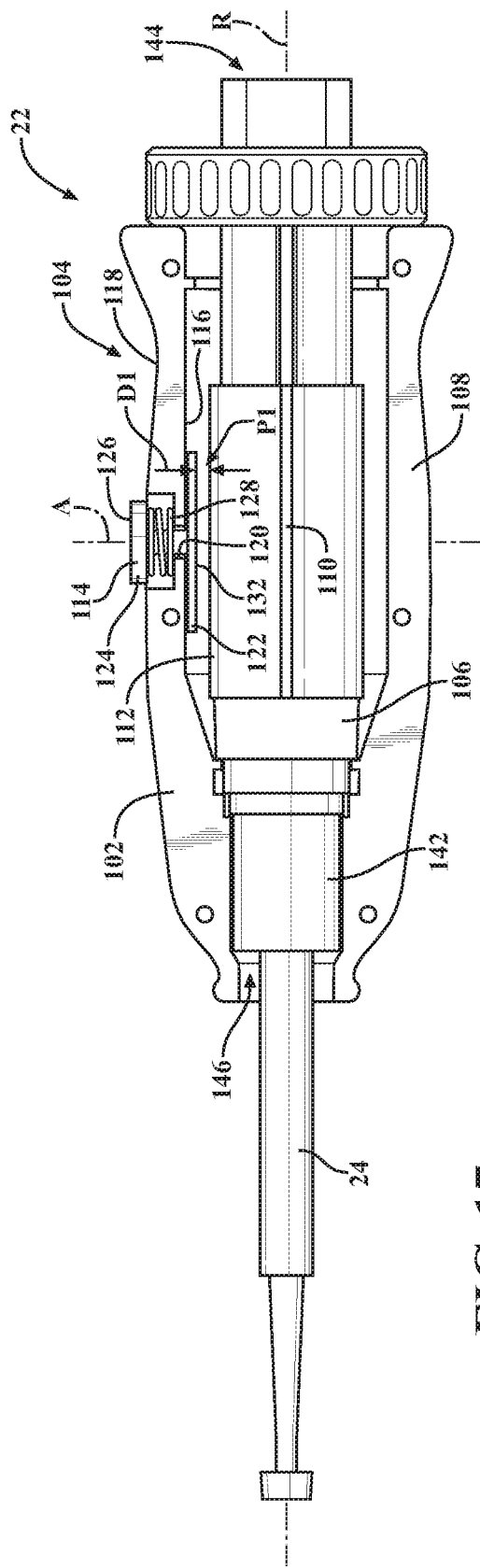
FIG. 17 is an elevational view of the end effector of FIG. 15 according to one example, with a portion of handle removed to show the target in the first position spaced the first distance from the conductive element.
Figure 18:
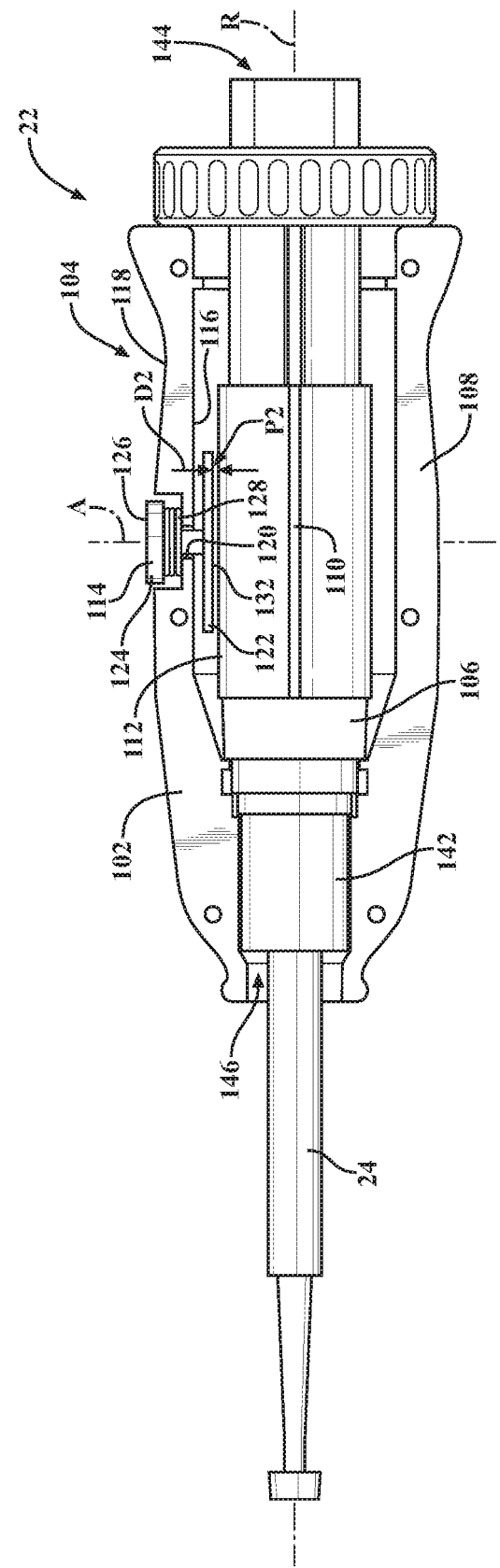
FIG. 18 is an elevational view of the end effector of FIG. 15 according to one example, with a portion of handle removed to show the target in the second position spaced the second distance from the conductive element.

The end effector 22 further comprises the target 114 mounted to and rotatable with the handle 102 and being movable relative to the handle 102 between the first position P1 (shown in FIG. 17) and the second position P2 (shown in FIG. 18). The target 114 is spaced apart from the conductive element 112 in both the first and second positions P1, P2 and is closer to the conductive element 112 in the second position P2 compared to the first position P1. The conductive element 112 is configured to sense the target 114 in the second position P2 for any rotational position between the first member 106 and the handle 102.

Additional details pertaining to the sensor system 104 are set forth in the description below. The details pertaining to the sensor system 104 may also be applicable to the end effector 22 (i.e., the application of the sensor system 104 in the end effector 22 as described above). However, the sensor system 104 is not limited to application with the end effector 22 as described herein. The sensor system 104 may be used in any suitable application that utilizes adjustable rotational positions between two components as well as sensing movement of a target 114 movably mounted to one of the components.

In one example, the second member 108 is configured to rotate around the first member 106 about the rotational axis R, as shown in FIGS. 8, 9, 13, and 14. Said differently, the second member 108 is disposed around the first member 106 along the rotational axis R. The first member 106 is fixed and the second member 108 rotates around the first member 106.

In another example, the first member 106 is configured to rotate around the second member 108 about the rotational axis R. Said differently, the first member 106 is disposed around the second member 108 along the rotational axis R. The second member 108 is fixed and the first member 106 rotates around the second member 108. The description below includes details and references to Figures showing the second member 108 configured to rotate around the first member 106 about the rotational axis R. However, the description below may be applied to the first member 106 configured to rotate around the second member 108 about the rotational axis R.

Although the first and second members 106, 108 are shown in the Figures as having concentric relationships along the rotational axis R, the first and second members 106, 108 may by non-concentric. For example, each of the first and second members 106, 108 may be disposed along and spaced from one another along the rotational axis R, with the first and second members 106, 108 extending orthogonally from rotational axis R. In this configuration, the first and second members 106, 108 are substantially parallel to one another orthogonal to the rotational axis R. Said differently, the first and second members 106, 108 are stacked along rotational axis R. The position of the first and second members 106, 108 may be reversed (i.e., the first member 106 may be above the second member 108 or the second member 108 may be above the first member 106). The rotational position between the first member 106 and the second member 108 is adjustable, but one of the members 106, 108 does not rotate around the other one of the members 106, 108. In this example, the surface 110 of the first member 106 is still disposed circumferentially about the rotational axis R. However, the surface 110 has a planar configuration orthogonal to the rotational axis R. The conductive element 112 is disposed on and fixed to the surface 110 of the first member 106, with the rotational axis R extending orthogonally through the conductive element 112 such that the conductive element 112 is disposed about the rotational axis R.

As shown in FIGS. 8, 9, 13, and 14, the second member 108 may define an interior surface 116, an exterior surface 118 opposite the interior surface 116 and a hole 120 extending from the interior surface 116 to the exterior surface 118, with the target 114 extending through the hole 120. More specifically, when the sensor system 104 is used with the end effector 22, the handle 102 may define the interior surface 116, the exterior surface 118, and the hole 120, as shown in FIGS. 17 and 18. The target 114 may extend past the interior and exterior surfaces 116, 118 such that the target 114 may be at least partially disposed in an interior and/or exterior of the second member 108. More specifically, the target 114 may include an interior portion 122 at least partially disposed in the interior of the second member 108. Furthermore, the target 114 may include an exterior portion 124 at least partially disposed in the exterior of the second member 108. In one example, the interior portion 122 is configured to face the conductive element 112, with the conductive element 112 configured to sense the interior portion 122 of the target 114 in the second position P2. In another example (e.g., such as when the first member 106 is configured to rotate around the second member 108 about the rotational axis R), the exterior portion 124 is configured to face the conductive element 112, with the conductive element 112 configured to sense the exterior portion 124 of the target 114 in the second position P2.

As shown in FIGS. 8, 9, 13, 14, 17 and 18, the portion of the target 114 not facing the conductive element 112 may be configured for engagement by an operator, mechanical actuator, or any other suitable device for facilitating movement of the target 114 between the first and second positions P1, P2. More specifically, when the interior portion 122 of the target 114 is configured to face the conductive element 112, the exterior portion 124 of the target 114 may be configured for engagement. Likewise, when the exterior portion 124 of the target 114 is configured to face the conductive element 112, the interior portion 122 of the target 114 may be configured for engagement. For example, the end effector 22 in FIGS. 15 and 16 further comprises a tactile interface 126 coupled to the handle 102, with the target 114 movable relative to the handle 102 between the first position P1 and the second position P2 responsive to actuation of the tactile interface 126. More specifically, the tactile interface 126 of the end effector 22 is the exterior portion 124 of the target 114. In this example, the tactile interface 126 is configured as a button for linear actuation of the target 114 by the operator. However, the tactile interface 126 may a separate component actuating the target 114. Furthermore, tactile interface 126 may be any portion of the target 114 and may actuate the target 114 between the first and second positions P1, P2 in any suitable manner. The tactile interface 126 may have any suitable configuration besides those described herein.

As shown in FIGS. 8, 9, 13, 14, 17, and 18, the target 114 may be configured to move linearly along a target axis A between the first and second positions P1, P2. The target axis A may be orthogonal to the rotational axis R. Furthermore, the target axis A may be radial to the rotational axis R. As such, movement of the target 114 between the first and second positions P1, P2 may result in movement of the target 114 normal to the conductive element 112 disposed about the rotational axis R, which facilitates the greatest change in distance between the target 114 and the conductive element 112 for the least amount of distance traveled by the target 114. When the hole 120 is present and the target 114 extends therethrough, the hole 120 may be aligned with the target axis A and the target 114 may move linearly within the hole 120 along the target axis A between the first and second positions P1, P2. The target axis A may be non-orthogonal to the rotational axis R and the target 114 may move in any non-linear path between the first and second positions P1, P2 without deviating from the scope of the subject invention.

The sensor system 104 may further include a biasing member 128 engaging each of the second member 108 and the target 114 and configured to bias the target 114 towards the first position P1. More specifically, when the sensor system 104 is used with the end effector 22 (as shown in FIGS. 17 and 18), the end effector 22 may further include the biasing member 128 engaging each of the handle 102 and the target 114 and being configured to bias the target 114 towards the first position P1. The biasing member 128 may be a compression spring disposed between the second member 108 and the target 114. For example, in one example the biasing member 128 abuts each of the exterior surface 118 of the second member 108 and the exterior portion 124 of the target 114. The biasing member 128 (configured as a compression spring) compresses during movement of the target 114 from the first position P1 to the second position P2. When the force moving the target 114 to the second position P2 is removed, the bias exerted by the biasing member 128 through the compression of the biasing member 128 moves the target 114 back to the first position P1. As such, the biasing member 128 may configure the target 114 to be normally disposed in the first position P1, with movement of the target 114 to the second position P2 being facilitated by external force exerted on the target 114 (by an operator, mechanical actuator, or any other suitable device as described above). The biasing member 128 may be any suitable configuration and may abut any portions of the target 114 and second member 108 for biasing the target 114 towards the first position P1.

Alternatively, the biasing member 128 may be configured to bias the target 114 towards the second position P2. As such, the biasing member 128 may configure the target 114 to be normally disposed in the second position P2 and sensed by the conductive element 112, with movement of the target 114 to the first position P1 being facilitated by external force exerted on the target 114 (by an operator, mechanical actuator, or any other suitable device as described above). The conductive element 112 may not sense the target 114 when it is moved to the first position P1 or may sense the target 114 differently in the first position P1 than the second position P2 (both scenarios discussed in greater detail below), which would be a detectable event for the conductive element 112.

As shown in FIGS. 4, 8, 9, 13, 14, and 16, the conductive element 112 may be disposed circumferentially about the surface 110. Said differently, the conductive element 112 may be wrapped around the rotational axis R and may lie along the surface 110 of the first member 106. Furthermore, the conductive element 112 may be concentric or orthogonal with the rotational axis R. In one example, the conductive element 112 may be disposed on or in a substrate 130 that is configured to flex circumferentially about the surface 110. The conductive element 112 is shown in FIGS. 5-14 to be disposed on or within the substrate 130. In the examples shown in FIGS. 5-14, the substrate 130 has a substantially rectangular shape and is wrapped around the rotational axis R such that opposing ends of the substrate 130 and face one another. The opposing ends of the substrate 130 may be spaced from one another, as shown in FIGS. 5, 8, 9, 10, 13, and 14. Alternatively, the opposing ends of the substrate 130 may abut one another or may overlap one another. In any of the examples, the conductive element 112 may be positioned within or along a majority of the substrate 130. As such, regardless of the disposition of the ends of the substrate 130, the conductive element 112 may be positioned substantially around the rotational axis R for sensing the target 114 in the second position P2 for any rotational position between the first member 106 and the second member 108.

As shown in FIGS. 8, 9, 13, and 14, the target 114 may comprise a detection surface 132 facing the surface 110 and/or conductive element 112. The detection surface 132 may have an arcuate configuration. Furthermore, the detection surface 132 may be concentrically aligned with the conductive element 112. The detection surface 132 can be a surface of the interior portion 122 of the target 114. As shown in the Figures, the detection surface 132 is the surface of the target 114 that is closest to the conductive element 112 in the second position P2. As such, the conductive element 112 senses the detection surface 132 of the target 114 in the second position P2. The arcuate configuration of the detection surface 132 concentrically aligned with the conductive element 112 facilitates even spacing between the target 114 and the conductive element 112 along the entire detection surface 132. Furthermore, the arcuate configuration of the detection surface 132 increases the detectable surface area of the target 114 (compared to a point or planar surface that progressively extends away from the concentric conductive element 112) which prevents the conductive element 112 inadvertently not sensing the target 114 in the second position P2.

In the example where the second member 108 is configured to rotate around the first member 106 about the rotational axis R, the detection surface 132 may have a concave configuration, as shown in FIGS. 8, 9, 13, and 14. In the example where the first member 106 is configured to rotate around the second member 108 about the rotational axis R, the detection surface 132 may have a convex configuration.

The rotational position between the first member 106 and the second member 108 may be freely rotatable throughout 360 degrees, or more, of rotation about the rotational axis R. The target 114 is spaced apart from the conductive element 112 in the first and second positions P1, P2 throughout the 360 degrees of rotation. More specifically, when the sensor system 104 is used with the end effector 22, the rotational position between the first member 106 and the handle 102 may be freely rotatable throughout 360 degrees of rotation about the rotational axis R. The target 114 is spaced apart from the conductive element 112 in the first and second positions P1, P2 throughout the 360 degrees of rotation. The conductive element 112 senses the target 114 in the second position P2 for all 360 degrees of rotation between the first member 106 and the second member 108 about the rotational axis R.

Figure 8:
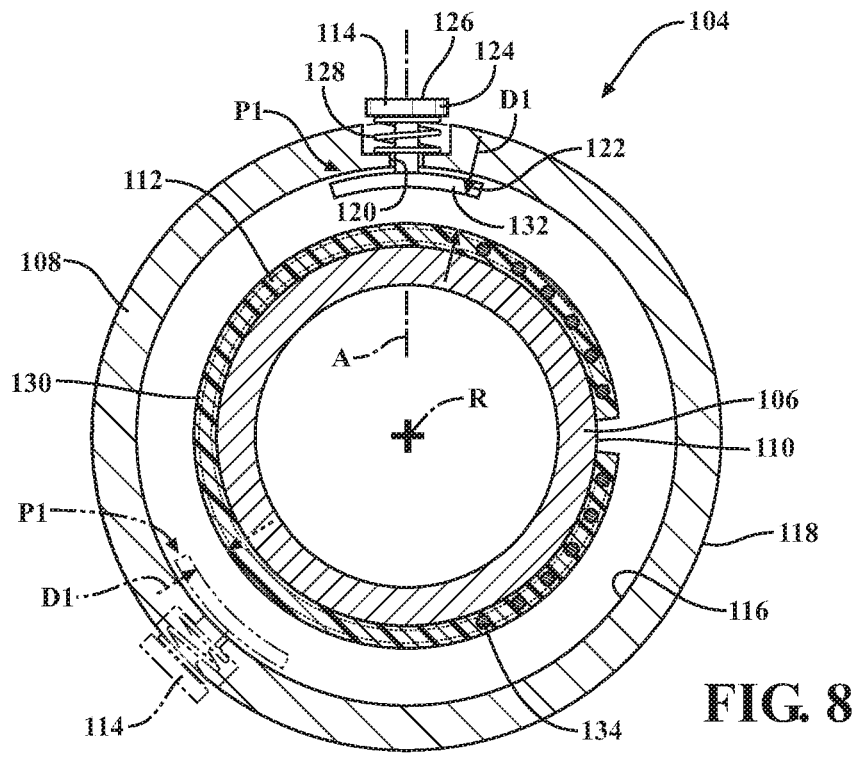
FIG. 8 is a cross-sectional view of the sensor system comprising the conductive element shown in FIG. 5 according to one example, with the target shown in two locations to depict rotation of the target and the second member around a rotational axis, and with the target in a first position spaced a first distance from the conductive element.
Figure 9:
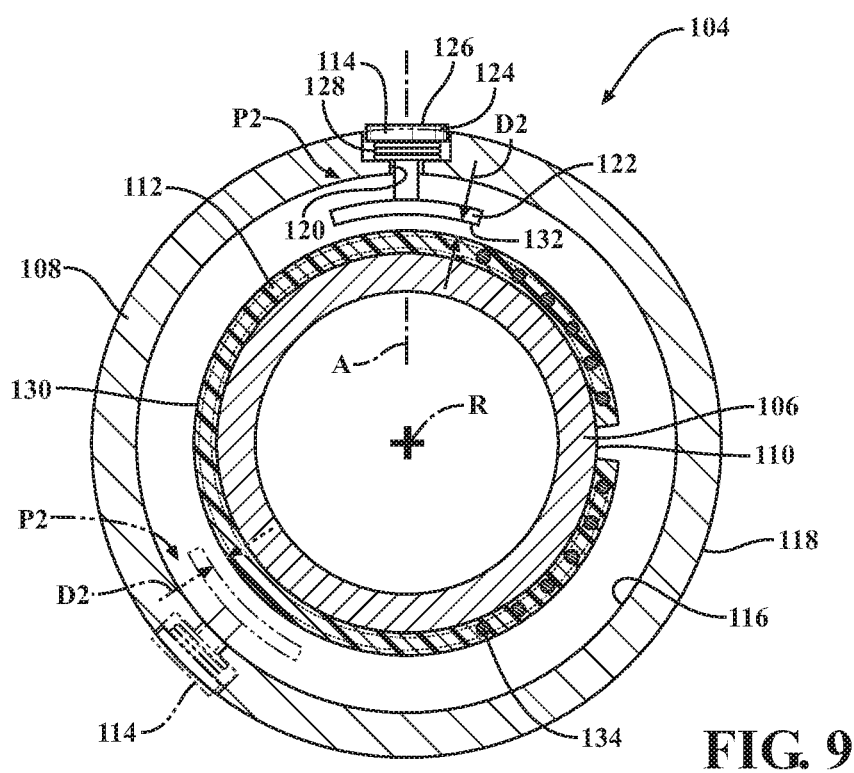
FIG. 9 is a cross-sectional view of the sensor system comprising the conductive element shown in FIG. 5 according to one example, with the target shown in two locations to depict rotation of the target and the second member around a rotational axis, and with the target in a second position spaced a second distance from the conductive element.
Figure 10:
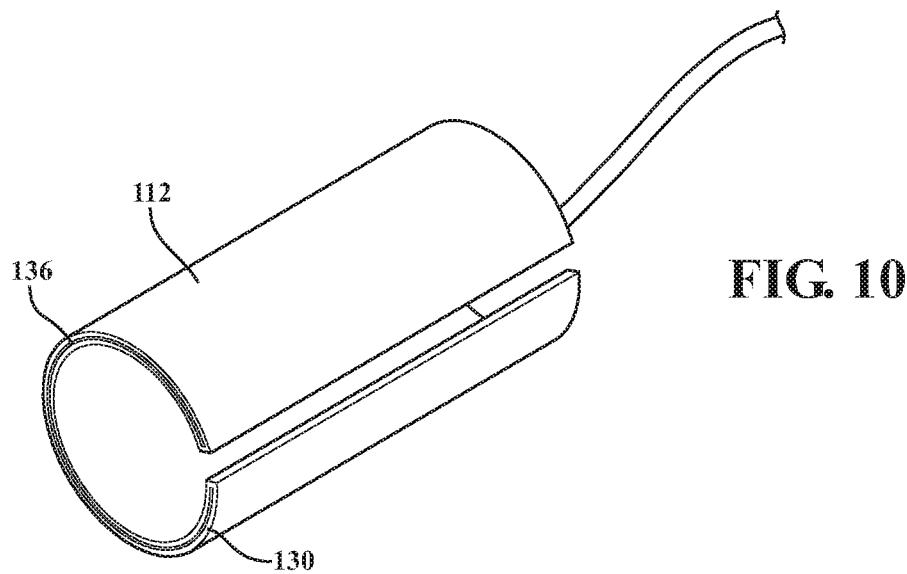
FIG. 10 is a perspective view of the conductive element comprising a capacitive plate and a substrate, according to one example.
Figure 11:
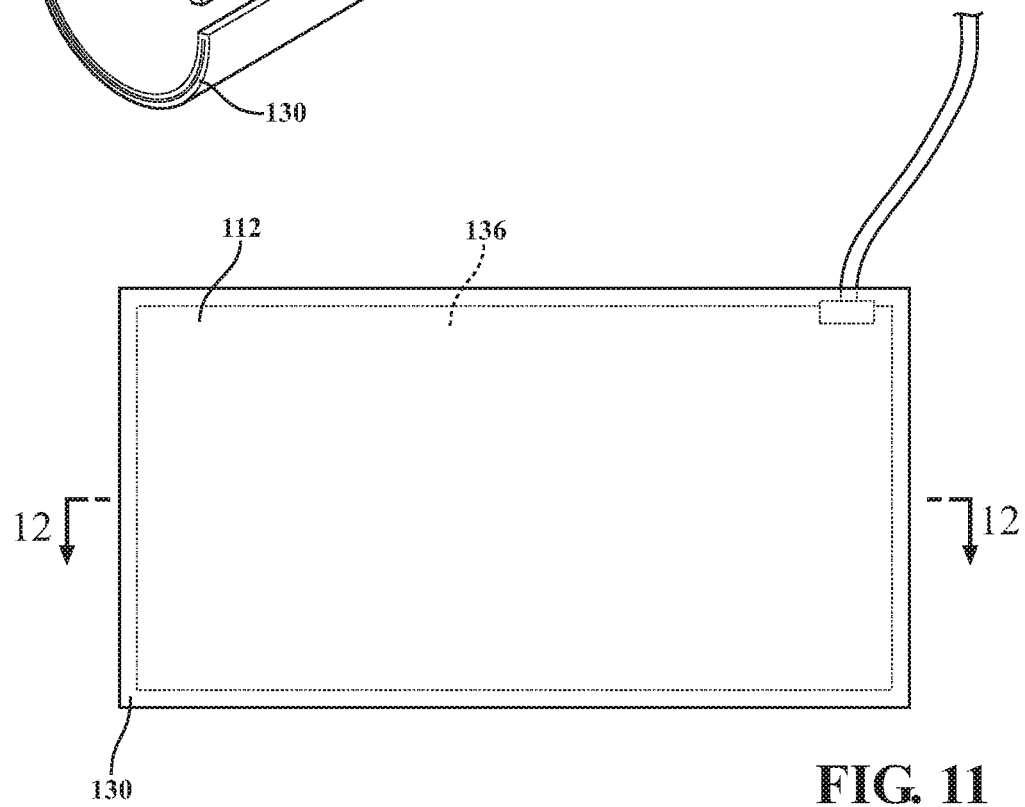
FIG. 11 is an elevational view of the conductive element shown in FIG. 10, unrolled into a planar configuration.
Figure 12:
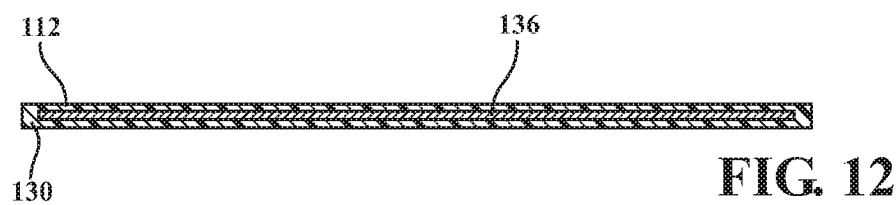
FIG. 12 is a cross-sectional view of the conductive element shown in FIG. 11 taken along line 12-12.
Figure 13:
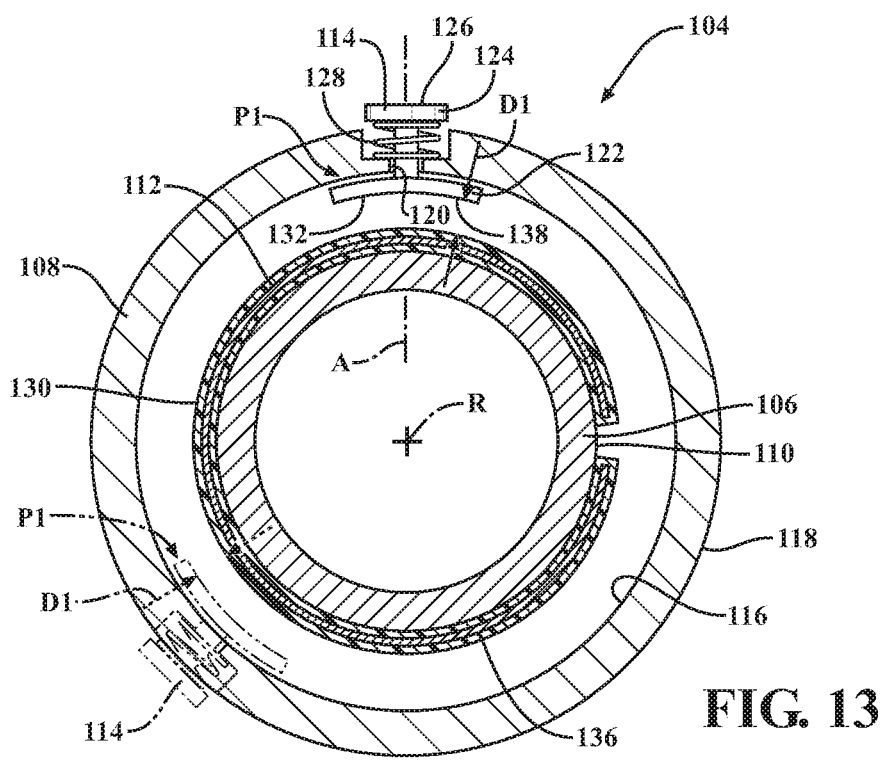
FIG. 13 is a cross-sectional view of the sensor system comprising the conductive element shown in FIG. 10 according to one example, with the target shown in two locations to depict rotation of the target and the second member around the rotational axis, and with the target in the first position spaced the first distance from the conductive element.
Figure 14:
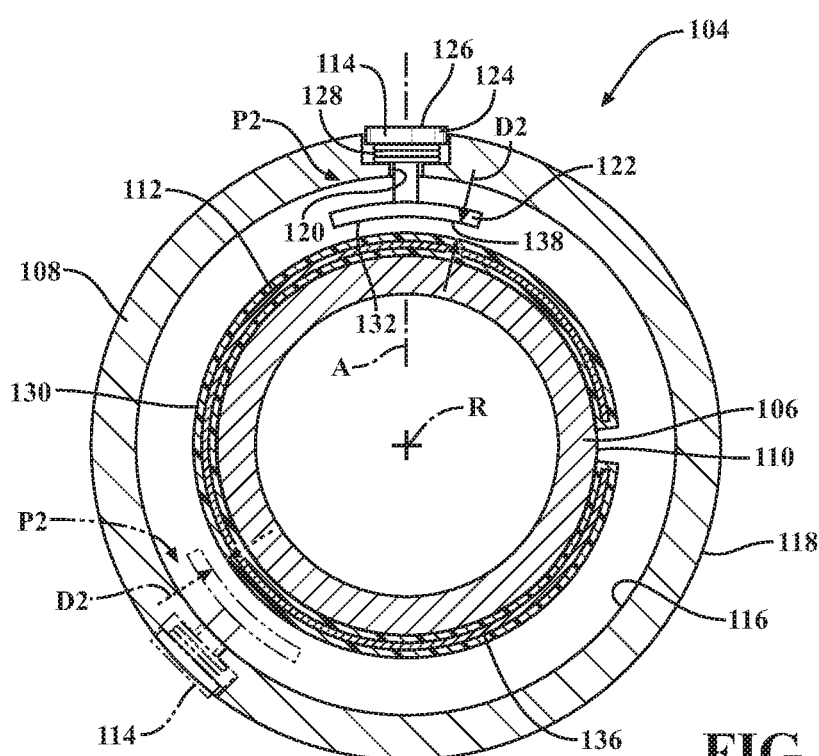
FIG. 14 is a cross-sectional view of the sensor system comprising the conductive element shown in FIG. 10 according to one example, with the target shown in two locations to depict rotation of the target and the second member around the rotational axis, and with the target in the second position spaced the second distance from the conductive element.

The target 114 in the first position P1 may be spaced apart from the conductive element 112 by a first distance D1 that is constant for any rotational position between the first member 106 and the second member 108, as shown in FIGS. 8 and 13. Furthermore, the target 114 in the second position P2 may be spaced apart from the conductive element 112 by a second distance D2 that is constant for any rotational position between the first member 106 and the second member 108, as shown in FIGS. 9 and 14. The second distance D2 may be less than the first distance D1. More specifically, when the sensor system 104 is used with the end effector 22, the target 114 in the first position P1 may be spaced apart from the conductive element 112 by the first distance D1 that is constant for any rotational position between the first member 106 and the handle 102, as shown in FIG. 17. Furthermore, the target 114 in the second position P2 may be spaced apart from the conductive element 112 by the second distance D2 that is constant for any rotational position between the first member 106 and the handle 102, as shown in FIG. 18. The second distance D2 may be less than the first distance D1. Said differently, the first distance D1 and the second distance D2 are constant for all rotational positions between the first and second members 106, 108. As such, the conditions for the conductive element 112 sensing the target 114 in the second position P2 is same for any rotational position between the first member 106 and the second member 108.

The target 114 being spaced apart from the conductive element 112 by the first distance D1 in the first position P1 and the second distance D2 in the second position P2 for any rotational position between the first member 106 and the second member 108 may be facilitated by details of the sensor system 104 described above. For example, the conductive member disposed circumferentially about the surface 110 of first member 106 and the detection surface 132 of the target 114 facing the surface 110 and having the arcuate configuration facilitates the conductive member and the target 114 maintaining concentric alignment as the first and second members 106, 108 adjust between the rotational positions. Because the conductive member and the target 114 are configured to maintain concentric alignment, the first and second distances D1, D2 are constant for any rotational position between the first member 106 and the second member 108.

As described above and shown in FIGS. 8, 9, 13, 14, 17, and 18, the target 114 is spaced apart from the conductive element 112 in both the first and second positions P1, P2. As such, the target 114 and the conductive do not contact one another. More specifically, the conductive element 112 does not sense the target 114 in the second position P2 by direct physical contact between the conductive element 112 and the target 114 or indirect physical contact between the conductive element 112 and the target 114 through an intermediate conductive component (such as a wire). Instead, the conductive element 112 is configured to wirelessly sense the target 114 in the second position P2. Wireless sensing between the target 114 and the conductive element 112 eliminates friction between the target 114 and the conductive element 112. Furthermore, when used with the end effector 22, the non-contact, disconnected configuration between the target 114 and the conductive element 112 allows for disassembly of the handle 102 and the target 114 from the first member 106 and the conductive element 112, which improves cleaning and sterilization of the end effector 22.

The sensor system 104 of the end effector 22 is coupled to the controller 30 (described in the overview above and shown in FIG. 2). The controller 30 may be configured to enable a command for controlling the end effector 22 responsive to the controller 30 identifying that the conductive element 112 senses the target 114 (e.g., the second position P2). The command may be one or more of: enabling or disabling the energy applicator 24, modifying a cutting speed of the energy applicator 24, modifying a feed rate of the end effector 22, and altering an orientation of the end effector 22 relative to the robotic manipulator 14. This list of commands is non-limiting. The controller 30 may be configured to enable other commands for controlling the end effector 22 not included herein.

In one example, the conductive element 112 utilizes binary sensing by producing an "on" signal when the conductive element 112 senses the target 114 in the second position P2, which is sent to the controller 30 when used with the end effector 22. When the target 114 is in the first position P1, the conductive element 112 may not sense the target 114 and the conductive element 112 produces a corresponding "off" signal, which is sent to the controller 30 when used with the end effector 22. Hence, in this example, the conductive element 112 only produces two signals that respectively correspond with the first and second positions P1, P2. The first position P1 may be any position of the target 114 relative to the second member 108 where the conductive element 112 does not sense the target 114. In some instances, the biasing member 128 may bias the target 114 to be normally disposed in the second position P2 and sensed by the conductive element 112. Here, the conductive element 112 produces a corresponding "off" signal, which is sent to the controller 30 when used with the end effector 22. The conductive element 112 does not sense the target 114 when it is moved to the first position P1. The conductive element 112 produces a corresponding "on" signal in the first position P1, which is sent to the controller 30 when used with the end effector 22.

In one example, the off and on signals correspondingly turn on and turn off (enable or disable) any function related to the energy applicator 24 of the end effector 22, such as altering the feed rate (speed with which the end effector 22 moves) or cutting (rotational) speed of the energy applicator 24, altering the orientation of the energy applicator 24, and the like.

Alternatively, the conductive element 112 may utilize variable proximity sensing. With variable proximity sensing, the conductive element 112 senses between the first and second positions P1, P2. Said differently, the distance between the target 114 and the conductive element 112 varies between a plurality of discrete positions, and these discrete positions are sensed by the conductive element 112. In each of the positions, the conductive element 112 senses the target 114 and may produce a unique signal for each of the positions, which is sent to the controller 30 when used with the end effector 22. The uniqueness of the signal may result from the unique interaction between the target 114 and the conductive element 112 for each discrete distance. The variability of this sensing may be define any number of distinct signals corresponding to any number of discrete positions of the target 114 throughout the range between the first and second positions P1, P2. For example, the sensor may be configured to detect five discrete positions of the target 114.

Each of the unique signals generated using variable proximity sensing may be used by the controller 30 to enable a command for controlling the end effector 22 responsive to the controller 30. In one non-limiting example, the energy applicator 24 of the end effector 22 may be a cutting burr with movement of the target 114 corresponding to rotation of the cutting burr. The rotational speed of the cutting burr may correspondingly increase as the target 114 moves closer to the conductive element 112. In another non-limiting example, the end effector 22 may be configured to move along the workpiece that is being cut. The feed rate of the cutting burr may correspondingly increase as the target 114 moves closer to the conductive element 112. Variable proximity sensing may be utilized for any suitable purpose with the end effector 22 or in any other application of the sensor system 104.

In one example (shown in FIGS. 5-9), the conductive element 112 comprises a conductive coil 134 configured to produce an electromagnetic field, and the target 114 comprises a metallic material configured to alter the electromagnetic field. The conductive element 112 is configured to inductively sense the target 114 in the second position P2. More specifically, an electric current passes through the conductive coil 134 and the electromagnetic field is produced. When the target 114 is in the second position P2, the metallic material alters the electromagnetic field, which changes the inductance of the conductive coil 134. The presence of target 114 in the second position P2 increases the current flowing through the conductive coil 134, which is sensed by the controller 30. The target 114 may comprise a magnetic material or any other material that can alter the electromagnetic field to produce a meaningful signal.

The conductive coil 134 may be wound in a spiral configuration within or along the substrate 130. Furthermore, the conductive coil 134 is disposed around the rotational axis R when the first and second members 106, 108 that are concentrically aligned. The conductive coil 134 may have any other configuration or geometry for enabling inductive sensing. For example, when the first and second members 106, 108 are non-concentric as described above (i.e., stacked), the conductive coil 134 may be wound along a plane defined by the surface 110 of the first member 106.

In another example (shown in FIGS. 21-23), the conductive coil 134 is configured to produce a variable electromagnetic field or varying inductance along the length of the rotational axis R. In this example, the controller 30 can distinguish between or separately identify different targets 114 along the rotational axis R. Alternatively, with this configuration, the controller 30 can distinguish between or separately identify different positions of one target 114 along the rotational axis R.

As described above, the target 114 is configured to alter the electromagnetic field and the conductive element 112 is configured to inductively sense the target 114 in the second position P2. When the target 114 is in the second position P2, the target 114 alters the electromagnetic field, which changes the inductance of the conductive coil 134. The presence of target 114 in the second position P2 increases the current flowing through the conductive coil 134, which is sensed by the controller 30.

By using the variable magnetic field, an additional level of detection of the target 114 is provided. The position of the target 114 along the rotational axis R may produce a uniquely identifiable current flowing through the conductive coil 134 (when the target is in the second position P2) that can be correlated with the position of the target 114 along the rotational axis R. More specifically, the current may vary depending on the position of the target 114 along the rotational axis R. The controller 30 may sense and distinguish both the variation of the target 114 between the first and second positions P1, P2, as well as the position of the target 114 along the rotational axis R and may produce and a separate and distinct signal for each of these positions.

Figure 19:
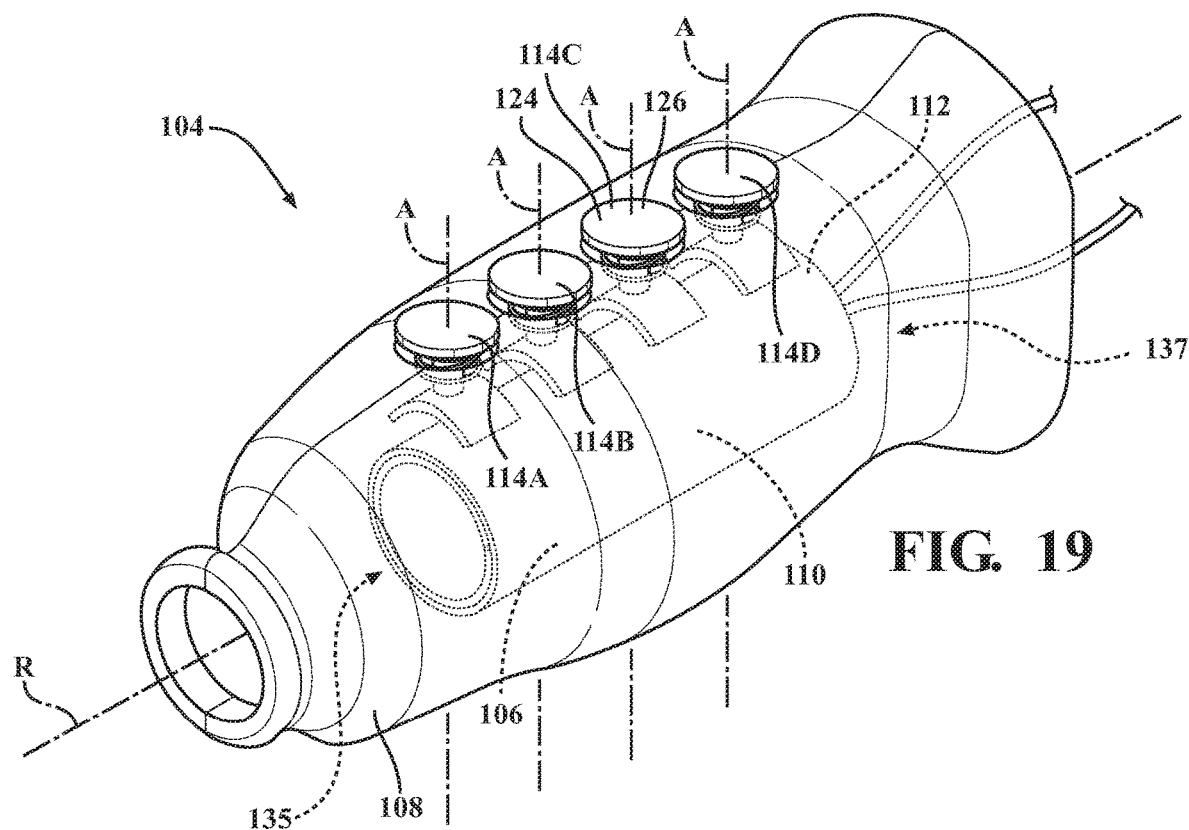
FIG. 19 is a perspective view of a sensor system showing a second member and four targets, according to one example.
Figure 20:
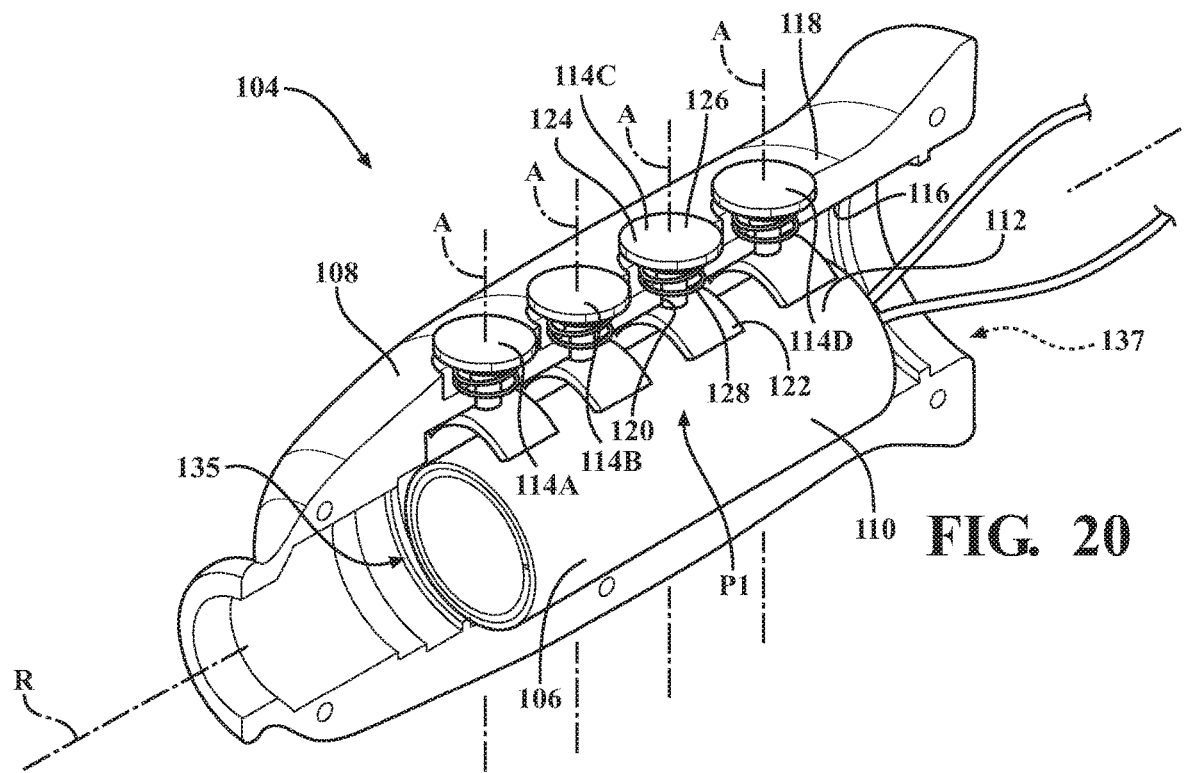
FIG. 20 is a perspective view of the sensor system shown in FIG. 19, with a portion of the second member removed to show a first member and a conductive element.

In one example, the production of various changes in current (i.e., changes in inductance) may be facilitated through the use of a plurality of targets 114 (e.g., four targets 114A-D as shown in FIGS. 19 and 20) that are spaced from one another along the rotational axis R. The targets 114 may be aligned (in a row) or may be aligned in other configurations. In another example, one or more targets 114 may be configured to slide along the rotational axis R between fixed positions.

Furthermore, the production of various changes in current (i.e., changes in inductance) may be facilitated by the conductive coil 134 being wound in a spiral configuration within or along the substrate 130. Windings of the coil 134 are varied in density or spacing along the rotational axis R to produce the variable electromagnetic field. In the examples shown in the Figures, the conductive coil 134 is configured as a copper trace disposed on the substrate. However, the conductive coil 134 may be configured as a wire or any other suitable conductive material. Moreover, the conductive coil 134 may be configured as pair of conductive coils 134 spaced from and substantially parallel to one another and electrically coupled to another in series through the substrate 130.

Figure 21:
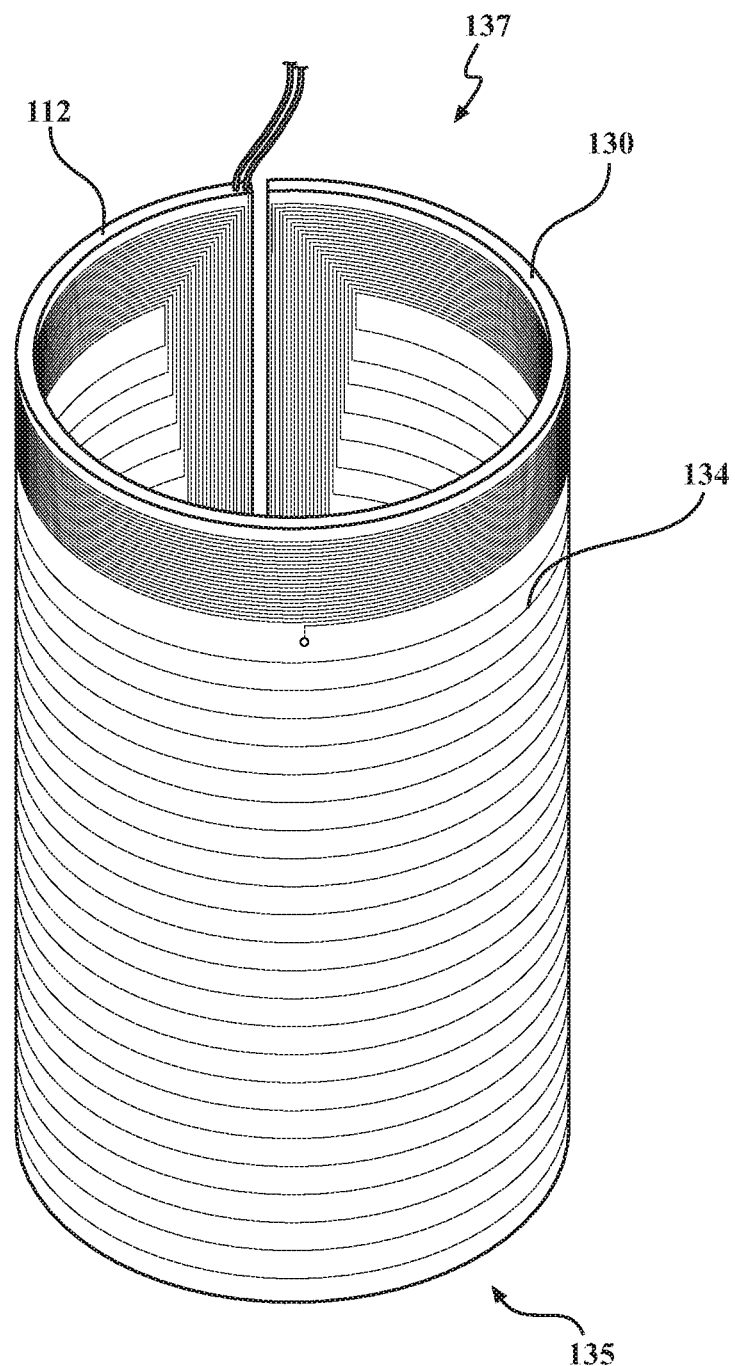
FIG. 21 is a perspective view of the conductive element shown in FIG. 20 comprising a conductive coil and a substrate, according to one example.
Figure 22:
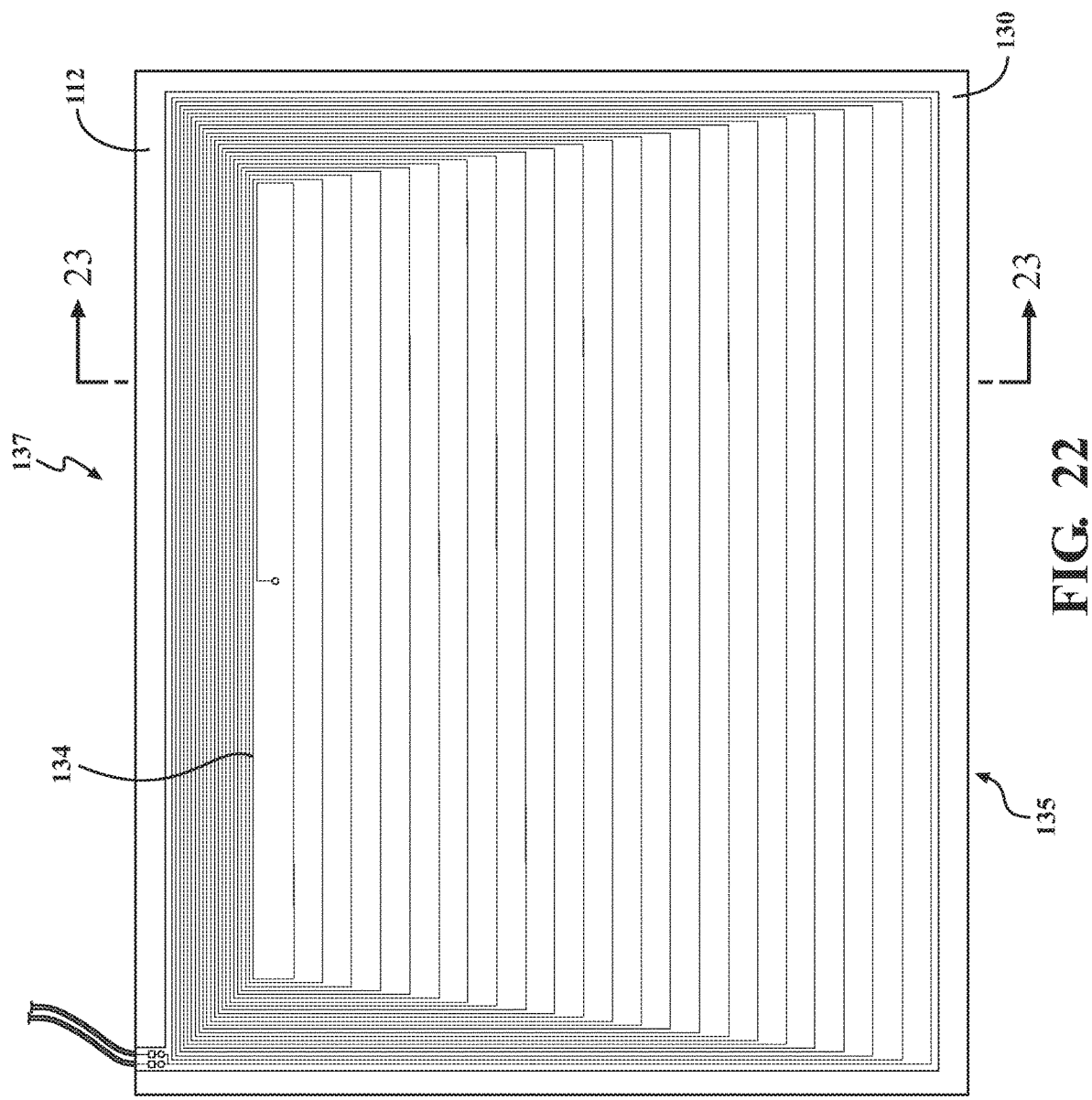
FIG. 22 is an elevational view of the conductive element shown in FIG. 21, unrolled into a planar configuration.

As shown in FIGS. 21-23, the conductive element 112 extends between a pair of ends 135, 137 along the rotational axis R. The spacing between the coil 134 is greater at one of the pair of ends 135 than the other one of the pair of ends 137. As such, each of the plurality of targets 114 spaced along the rotational axis would produce a different current flow in their respective second positions P2 because each of the targets 114 would short out a different number of turns of the coil 134. More specifically, as shown in FIGS. 19 and 20, target 114A is disposed at the end 135 of the conductive element having the greatest spacing between the coils 134 while targets 114B-D are progressively positioned closer to the end 137 of the conductive element 112 having the least spacing between the coils 134. As such, target 114A will short out fewer turns of the coil 134 in the second position P2 than target 114B in the second position P2 and will generate less change in inductance than target 114B. Target 114B will short out fewer turns of the coil 134 in the second position P2 than target 114C in the second position P2 and will generate less change in inductance than target 114C. Target 114C will short out fewer turns of the coil 134 in the second position P2 than target 114D in the second position P2 and will generate less change in inductance than target 114D. The controller 30 will sense and distinguish the variations in inductance between the first and second positions P1, P2 of each of the targets 114A-D and will produce and a separate and distinct signal for each of the targets 114A-D and their respective positions P1-P2.

In one example, the inductance of the conductive coil 134 may be measured using an LC tank circuit driven at resonance. As such, the controller 30 may measure a change in inductance, which is caused by a shift in the resonant frequency of the tank circuit and may produce a separate and distinct signal for each of the targets 114A-D and their respective positions P1-P2. However, the change in inductance may be performed using and any suitable method. The controller 30 may detect one or more targets 114 at a time. If multiple targets 114 are pressed at the same time, the controller 30 may detect the multiple targets 114 and prioritize one or more of the targets 114 according to any set of predetermined rules.

In yet another example, the conductive coil 134 is configured to produce a variable electromagnetic field or varying inductance about (e.g., circumferentially) the rotational axis R. This variable magnetic field configuration may be for purposes, such as to accommodate provide a variable signal for one or more targets 114 for different positions of the one or more targets 114 about the rotational axis R. In this example, the controller 30 can identify the relative position of the one or more targets 114 about the rotational axis R, instead of along the rotational axis R. The coil 134 in this configuration, for example, may be like shown in FIG. 21, but having the varied density coil windings orientated parallel to the rotational axis R, rather than perpendicular thereto. Any of the techniques described above may be utilized for this configuration.

In another example (shown in FIGS. 10-14), the conductive element 112 comprises a capacitive plate 136 and the target 114 comprises an opposing capacitive plate 138. The conductive element 112 is configured to capacitively sense the target 114 in the second position P2. More specifically, each of the plates are electrical conductors (e.g., electrodes) and are operable together to form a capacitor. An electric current is applied to the capacitive plate 136 of the conductive element 112 and generates a first electric charge therein. An electric current may be applied to the capacitive plate 138 of the target 114, which generates a second electric charge therein. Alternatively, the second electric charge may be generated by a conductive object touching the target 114 (such as a human finger). In such instances, the target 114 may be passive rather than actively charged. When the target 114 is in the second position P2, the plates of the target 114 and the conductive element 112 form a capacitor therebetween. The presence of, or change in, capacitance may be sensed by the controller 30.

The capacitive plate 136 of the conductive element 112 may have a circumferentially planar configuration. The capacitive plate 136 of the conductive element 112 may have any other configuration or geometry for enabling capacitive sensing. For example, when the first and second members 106, 108 are non-concentric as described above (i.e., stacked), the capacitive plate 136 may extend along a plane defined by the surface 110 of the first member 106.

Figure 15:
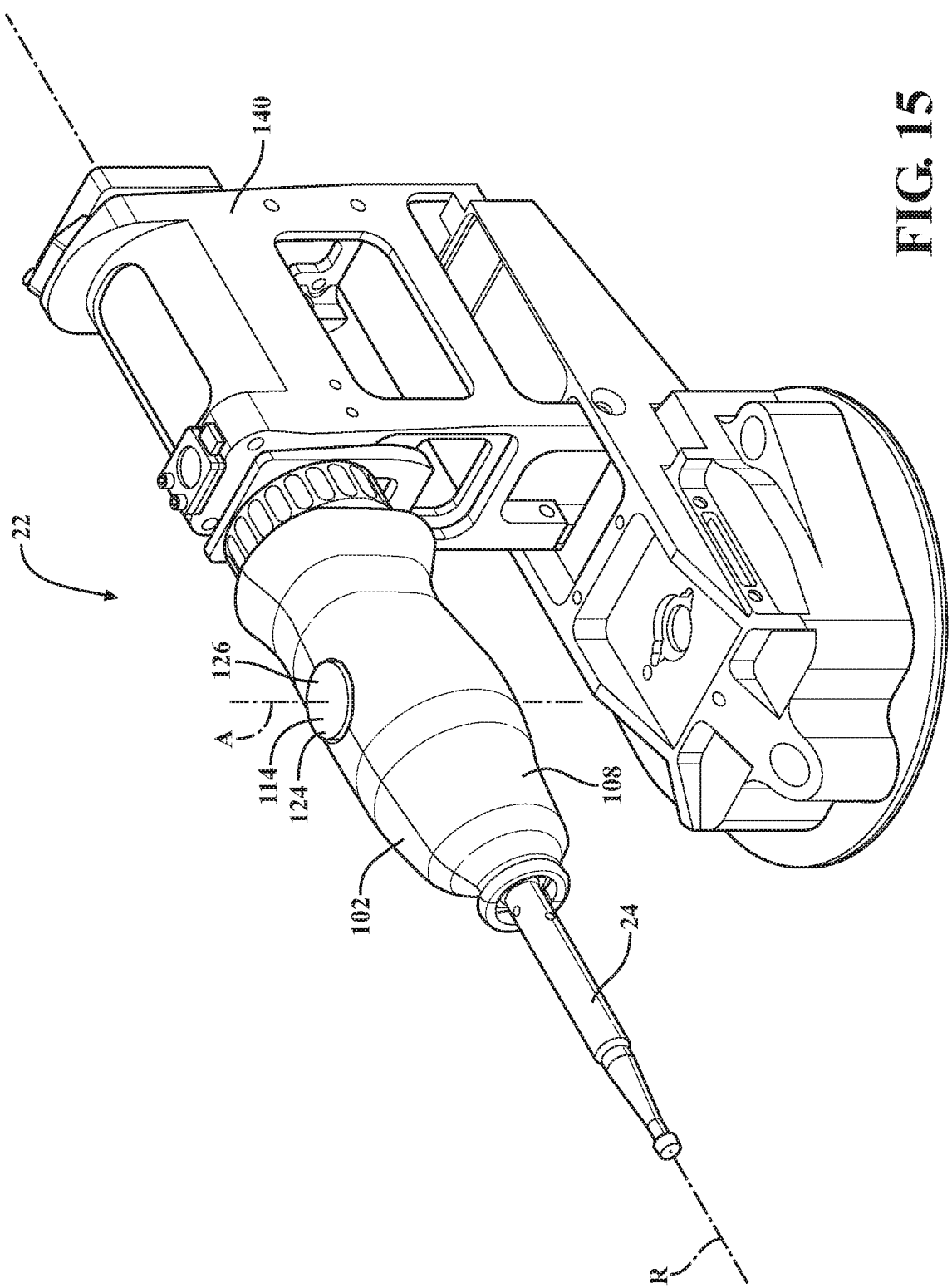
FIG. 15 is a perspective view of an end effector for use with the robotic system shown in FIG. 1, according to one example, and showing a handle, a mounting fixture, and an energy applicator.
Figure 16:
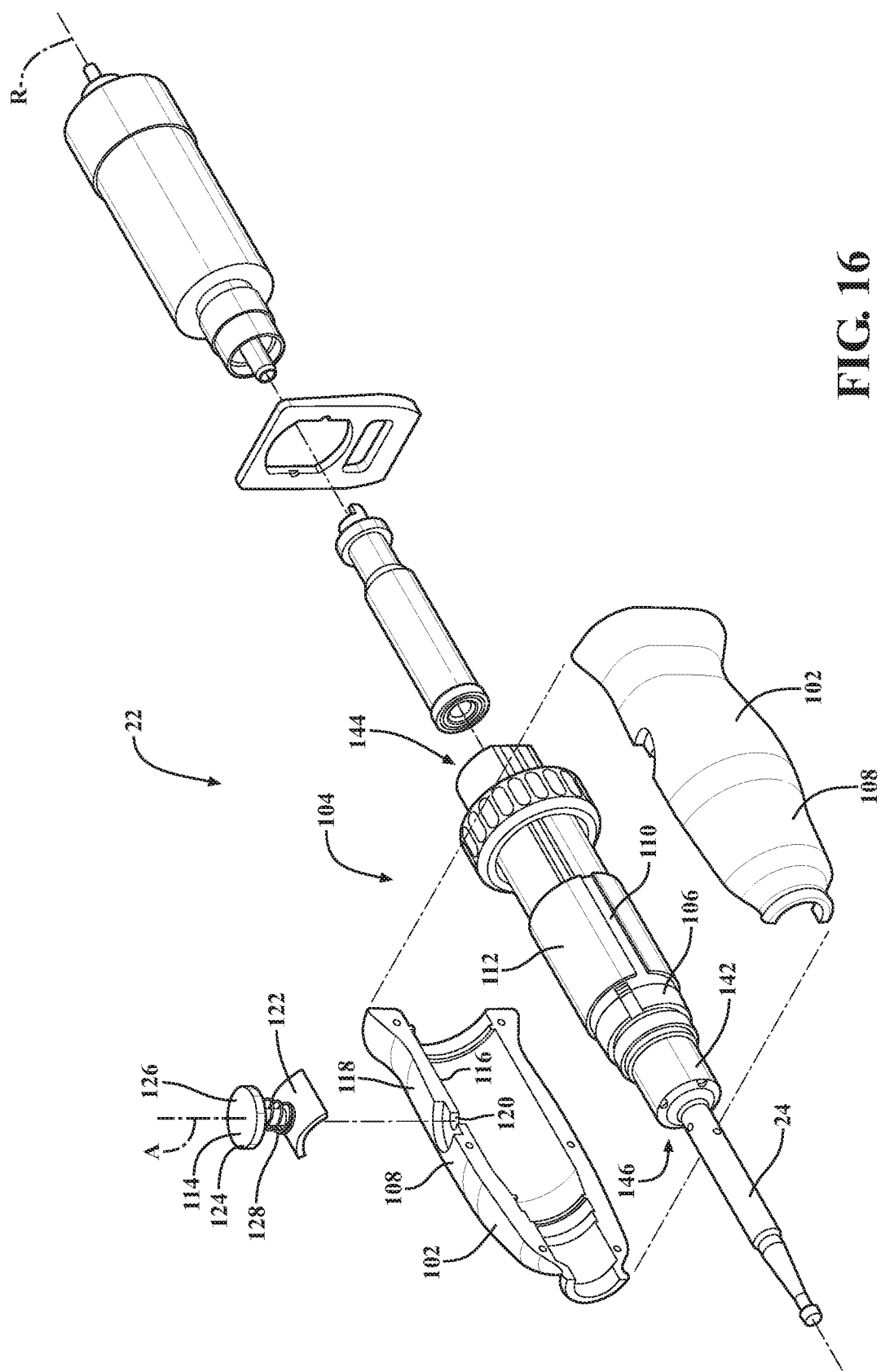
FIG. 16 is an exploded view of the end effector of FIG. 15 showing the sensor system used with the end effector, according to one example.

As shown in FIG. 15, the end effector 22 may further comprise a mounting fixture 140 for coupling the end effector 22 to the robotic manipulator 14. As shown in FIGS.

16-18, the first member 106 may include a nose tube 142 having a proximal end 144 adjacent to the mounting fixture 140 and an opposing distal end 146. The energy applicator 24 may extend beyond the distal end 146. The energy applicator 24 may be mounted to the distal end 146 of the nose tube 142. Alternatively, the energy applicator 24 may be mounted within the nose tube 142 and may extends through the distal end 146.

The nose tube 142 may be fixed to the mounting fixture 140, such that the first member 106 does not move relative to the mounting fixture 140. With the first member 106 fixed to the mounting fixture 140, the handle 102 (moreover, the second member 108 of the sensor system 104) rotates around the first member 106. In alternative examples, the second member 108 may be fixed to the mounting fixture 140 and the first member 106 may rotate around the second member 108.

Several examples have been described in the foregoing description. However, the examples discussed herein are not intended to be exhaustive or limit the invention to any particular form. The terminology, which has been used, is intended to be in the nature of words of description rather than of limitation. Many modifications and variations are possible in light of the above teachings and the invention may be practiced otherwise than as specifically described.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

The invention claimed is:

1. A sensor system comprising:
   a first member extending along a rotational axis and having a surface disposed circumferentially about the rotational axis;
   a conductive element fixed to the first member and disposed on the surface and disposed about the rotational axis;
   a second member extending along the rotational axis and with a rotational position between the first member and the second member being adjustable; and
   a target mounted to and rotatable with the second member and being movable relative to the second member between a first position and a second position, the target being spaced apart from the conductive element in both the first and second positions and being closer to the conductive element in the second position compared to the first position;
   wherein the conductive element is configured to sense the target in the second position for any rotational position between the first member and the second member.

2. The sensor system of claim 1, wherein the rotational position between the first member and the second member is freely rotatable throughout 360 degrees of rotation about the rotational axis, and wherein the target is spaced apart from the conductive element in the first and second positions throughout the 360 degrees of rotation.

3. The sensor system of claim 1, wherein the conductive element is disposed circumferentially about the surface.

4. The sensor system of claim 1, wherein the conductive element comprises a conductive coil configured to produce an electromagnetic field, and the target comprises a metallic material configured to alter the electromagnetic field and wherein the conductive element is configured to inductively sense the target in the second position.

5. The sensor system of claim 4, wherein the conductive coil is wound in a spiral configuration that varies in density along the rotational axis to produce a variable electromagnetic field along the rotational axis.

6. The sensor system of claim 5, further comprising a plurality of targets each being spaced at a different position from one another relative to the spiral configuration, wherein the conductive element is configured to utilize the variable electromagnetic field to individually sense any of the plurality of targets in the second position for any rotational position between the first member and the second member.

7. The sensor system of claim 1, wherein the conductive element comprises a capacitive plate and the target comprises an opposing capacitive plate and wherein the conductive element is configured to capacitively sense the target in the second position.

8. The sensor system of claim 1, wherein the conductive element is disposed on or in a substrate that is configured to flex circumferentially about the surface.

9. The sensor system of claim 1, further including a biasing member engaging each of the second member and the target and being configured to bias the target towards the first position.

10. The sensor system of claim 1, wherein the target comprises a detection surface facing the surface and having an arcuate configuration.

11. The sensor system of claim 1, wherein the target in the first position is spaced apart from the conductive element by a first distance that is constant for any rotational position between the first member and the second member, and wherein the target in the second position is spaced apart from the conductive element by a second distance that is constant for any rotational position between the first member and the second member the second distance being less than the first distance.

12. The sensor system of claim 1, wherein the second member defines an interior surface, an exterior surface opposite the interior surface and a hole extending from the interior surface to the exterior surface, with the target extending through the hole.

13. The sensor system of claim 1, wherein the target is configured to move linearly along a target axis between the first and second positions, the target axis being orthogonal to the rotational axis.

14. The sensor system of claim 1, wherein the second member is configured to rotate around the first member about the rotational axis.

15. The sensor system of claim 1, wherein the first member is configured to rotate around the second member about the rotational axis.

16. An end effector for a robotic manipulator, the end effector comprising:
   a first member extending along a rotational axis and having a surface disposed circumferentially about the rotational axis;
   an energy applicator disposed within the first member;
   a conductive element fixed to the first member and disposed on the surface and disposed about the rotational axis;
   a handle extending along the rotational axis and with a rotational position between the first member and the handle being adjustable; and a target mounted to and rotatable with the handle and being movable relative to the handle between a first position and a second position, the target being spaced apart from the conductive element in both the first and second positions and being closer to the conductive element in the second position compared to the first position;

wherein the conductive element is configured to sense the target in the second position for any rotational position between the first member and the handle.

17. The end effector of claim 16, comprising a mounting fixture for coupling the end effector to the robotic manipulator, and wherein the first member includes a nose tube having a proximal end adjacent to the mounting fixture and an opposing distal end, and wherein the energy applicator extends beyond the distal end.

18. The end effector of claim 16, wherein the rotational position between the first member and the handle is freely rotatable throughout 360 degrees of rotation about the rotational axis, and wherein the target is spaced apart from the conductive element in the first and second positions throughout the 360 degrees of rotation.

19. The end effector of claim 16, wherein the conductive element comprises a conductive coil configured to produce an electromagnetic field, and the target comprises a metallic material configured to alter the electromagnetic field and wherein the conductive element is configured to inductively sense the target in the second position.

20. The end effector of claim 19, wherein the conductive coil is wound in a spiral configuration that varies in density along the rotational axis to produce a variable electromagnetic field along the rotational axis.

21. The end effector of claim 20, further comprising a plurality of targets each being spaced at a different position from one another relative to the spiral configuration, wherein the conductive element is configured to utilize the variable electromagnetic field to individually sense any of the plurality of targets in the second position for any rotational position between the first member and the second member.

22. The end effector of claim 16, wherein the conductive element comprises a capacitive plate and the target comprises an opposing capacitive plate and wherein the conductive element is configured to capacitively sense the target in the second position.

23. The end effector of claim 16, further including a biasing member engaging each of the handle and the target and being configured to bias the target towards the first position.

24. The end effector of claim 16, wherein the target in the first position is spaced apart from the conductive element by a first distance that is constant for any rotational position between the first member and the handle, and wherein the target in the second position is spaced apart from the conductive element by a second distance that is constant for any rotational position between the first member and the handle, the second distance being less than the first distance.

25. The end effector of claim 16, wherein the handle defines an interior surface, an exterior surface opposite the interior surface and a hole extending from the interior surface to the exterior surface, with the target extending through the hole.

26. The end effector of claim 16, further comprising a tactile interface coupled to the handle and wherein the target is movable relative to the handle between the first position and the second position responsive to actuation of the tactile interface.

27. The end effector of claim 16, further comprising a controller configured to enable a command for controlling the end effector responsive to the controller identifying that the conductive element senses the target in the second position.

28. The end effector of claim 26, wherein the command is one or more of:
enabling or disabling the energy applicator;
modifying a cutting speed of the energy applicator;
modifying a feed rate of the end effector; and
altering an orientation of the end effector relative to the robotic manipulator.

29. A robotic system comprising:
a manipulator comprising a plurality of links; and
an end effector coupled to the manipulator and comprising:
a first member extending along a rotational axis and having a surface disposed circumferentially about the rotational axis;
an energy applicator disposed within the first member;
a conductive element fixed to the first member and disposed on the surface and disposed about the rotational axis;
a handle extending along the rotational axis and with a rotational position between the first member and the handle being adjustable; and
a target mounted to and rotatable with the handle and being movable relative to the handle between a first position and a second position, the target being spaced apart from the conductive element in both the first and second positions and being closer to the conductive element in the second position compared to the first position;
wherein the conductive element is configured to sense the target in the second position for any rotational position between the first member and the handle.

* * * * *